US009885686B2

United States Patent
Asare-Okai et al.

(10) Patent No.: US 9,885,686 B2
(45) Date of Patent: Feb. 6, 2018

(54) ELECTROPHORESIS CONTROLLERS, SENSORS, AND METHODS FOR CONTROLLING ELECTROPHORESIS PROCESSES

(71) Applicant: THE RESEARCH FOUNDATION FOR THE STATE UNIVERSITY OF NEW YORK, Albany, NY (US)

(72) Inventors: Papa Nii Asare-Okai, Slingerlands, NY (US); Rabi A. Musah, Albany, NY (US); Tony P. Hoang, Albany, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 539 days.

(21) Appl. No.: 14/520,624

(22) Filed: Oct. 22, 2014

(65) Prior Publication Data

US 2015/0083594 A1 Mar. 26, 2015
US 2017/0138897 A9 May 18, 2017

Related U.S. Application Data

(63) Continuation-in-part of application No. PCT/US2013/030220, filed on Mar. 11, 2013.
(Continued)

(51) Int. Cl.
*G01N 27/447* (2006.01)
(52) U.S. Cl.
CPC .................. *G01N 27/447* (2013.01)
(58) Field of Classification Search
CPC ....................................... G01N 27/447–27/453
See application file for complete search history.

(56) References Cited

U.S. PATENT DOCUMENTS 4,781,464 A 11/1988 Allington et al.
5,069,769 A 12/1991 Fujimiya et al.
(Continued)

FOREIGN PATENT DOCUMENTS

EP 0134622 3/1985
JP 2007155560 6/2007
(Continued)

OTHER PUBLICATIONS

R. R. Baddi, et al. "Use LEDs as photodiodes" EDN Network webpage, published Nov. 18, 2010.*
(Continued)

*Primary Examiner* — J. Christopher Ball
(74) *Attorney, Agent, or Firm* — Heslin Rothenberg Farley and Mesiti PC

(57) ABSTRACT

An electrophoresis controller for use with an electrophoresis apparatus having a gel matrix disposed between electrodes for separation of particles along with a tracking dye. The electrophoresis controller includes a sensor system and a controller. The sensor system includes a support, a light emitter, and a light receiver. The support includes a first portion positionable on a first side of the gel matrix and a second portion positionable adjacent a second side of the gel matrix. The light emitter is positioned on the first portion of the support for emitting light onto one side of the gel matrix. The light receiver is positioned on the second portion of the support adjacent to the other side of the gel matrix for receiving light from the light source as it is passing through the gel matrix. At least one of the light emitter and the light receiver includes a light guide having a first end and a second end. The first end is positioned on the support and facing the gel matrix, and the second end is remote from the sensor system. The controller is operably connected to the sensor for monitoring a change in the light from the illumi-
(Continued)

nated gel matrix due to migration of the tracking dye into the illuminated gel matrix and received by the light receiver.

44 Claims, 31 Drawing Sheets

Related U.S. Application Data

(60) Provisional application No. 61/713,294, filed on Oct. 12, 2012.

(56) References Cited

U.S. PATENT DOCUMENTS

| | | | |
|---|---|---|---|
| 5,104,512 A | 4/1992 | Gombocz et al. | |
| 5,120,419 A | 6/1992 | Papp | |
| 5,268,568 A | 12/1993 | Lee | |
| 6,068,753 A | 5/2000 | Sarrine et al. | |
| 6,379,516 B1 | 4/2002 | Cabilly et al. | |
| 7,967,968 B2 | 6/2011 | Kober et al. | |
| 2008/0142365 A1* | 6/2008 | Kober | G01N 27/44726 204/450 |
| 2011/0259744 A1* | 10/2011 | Moyle | G01N 27/44726 204/461 |

FOREIGN PATENT DOCUMENTS

| | | |
|---|---|---|
| KR | 20050006861 | 1/2005 |
| WO | 2014/058462 | 4/2014 |

OTHER PUBLICATIONS

International Search Report and Written Opinion, PCT Application Serial No. PCT/US2013/30220, published as WO2014/058462, 7-pages, dated Mar. 18, 2013.
Experion Automated Electrophoresis System, available from Bio-Rad Laboratories, Inc. Bulletin 3140 Rev F, 8-pages. Aug. 2011.
Bio-Rad Mini-Protean®, available from Bio-Rad Laboratories, Inc., printout available online by Manufacturing Chemist Pharmaon on Aug. 22, 2014, at http://www.manufacturingchemist.com/news/article_page/BioRad_adds_MiniProtean_TGX_precast_gels/46647, 4-pages, Mar. 12, 2010.
Wehr et al., "Experion Automated Electrophoresis System: Enhancing Sensitivity in SDS-Protein Electrophoresis", Bio-Rad Laboratiories, Inc., Bulletin 5719 Rev A, 6-pages, 2008.
Electrophoresis Power Supply from LA Biohackers, printout available on Oct. 2, 2012, at http://wiki.biohackers.la/electrophoresis_Power_Supply, 5 pages, Oct. 2, 2012.
International Report on Patentability, PCT Application Serial No. PCT/US2013/30220, published as WO2014/058462, 5-pages, dated Apr. 14, 2015.

* cited by examiner

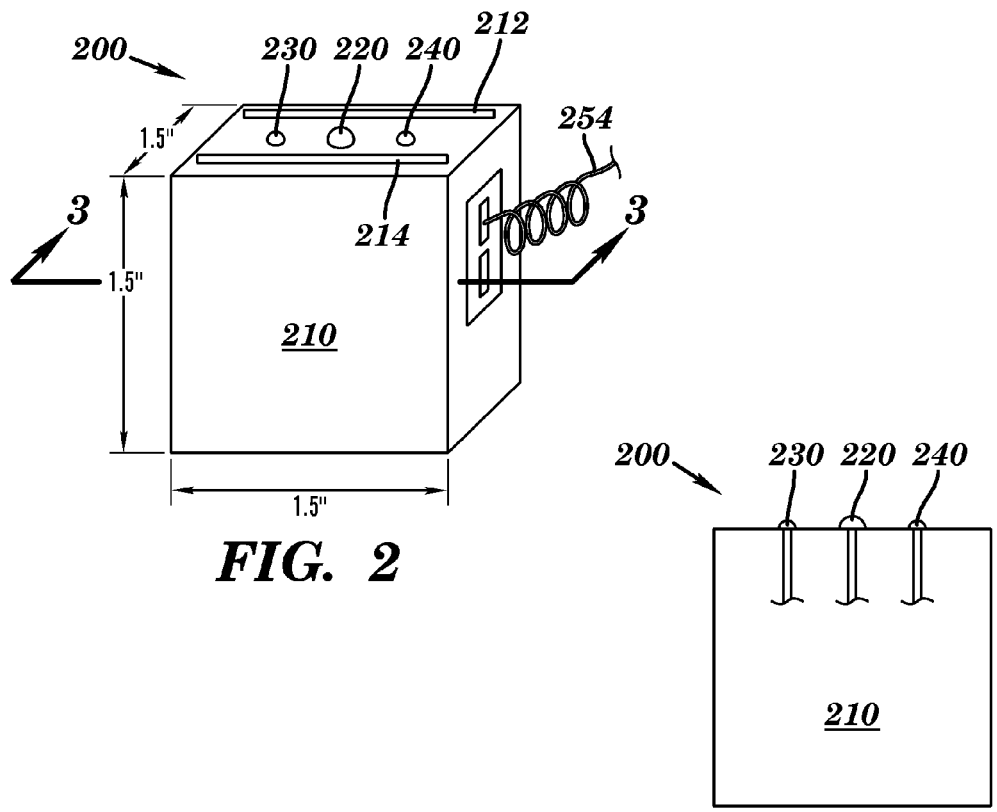
FIG. 2
FIG. 3
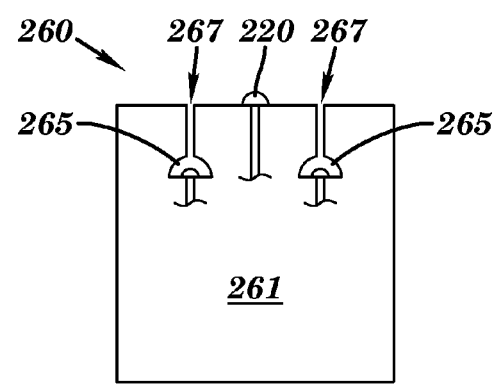
FIG. 4

ELECTROPHORESIS CONTROLLERS, SENSORS, AND METHODS FOR CONTROLLING ELECTROPHORESIS PROCESSES

CROSS-REFERENCE TO RELATED APPLICATIONS

This application is a continuation-in-part of PCT International Application No. PCT/US2013/30220, filed Mar. 11, 2013, entitled "Electrophoresis Controllers And Methods For Controlling Electrophoresis Process," which claims the benefit of U.S. Provisional Patent Application No. 61/713,294, filed Oct. 12, 2012, entitled "Electrophoresis Controllers And Methods For Controlling Electrophoresis Apparatus", which applications are hereby incorporated herein by reference in its entirety.

This application is related to concurrently filed and commonly assigned, provisional patent application Ser. No. 62/067,036, filed Oct. 22, 2014, by Asare-Okai et al., and entitled "Electrophoresis Controllers, Sensors, And Methods For Controlling Electrophoresis Processes," which is hereby incorporated herein by reference in its entirety.

FIELD OF THE INVENTION

This disclosure relates generally to electrophoresis and more specifically, to electrophoresis controllers and electrophoresis apparatus employing the same.

BACKGROUND OF THE INVENTION

Electrophoresis gels are widely used in biotechnology for analyzing biomolecular sample materials such as proteins and nucleic acids. In molecular biology research laboratories, it is well known to use gel electrophoresis to separate and identify sample material based on size, charge, and other aspects of the sample material. Biomolecules such as DNA, RNA, and protein are commonly separated using this procedure. Electrophoresis involves the migration of electrically charged particles in a gel solution or suspension in the presence of an applied electric field. Samples are inserted or loaded into the gel of an electrophoretic gel system (EGS) and thereafter an electric field is applied to the gel. Each particle in the sample moves toward the electrode having an electrical charge which is opposite the sign of charge of the particle. The electrophoretic mobility of a sample particle is inversely proportional to the size of the particle. Various species of a sample may be separated and identified due to differences in their electrophoretic mobilities in the gel.

U.S. Pat. No. 5,120,419 issued to Papp discloses a photoelectric electrophoresis controller triggered by molecular samples and/or molecular marker dyes sensed by photodetector means when reaching determined position in a matrix, characterized by an observing photocell spaced from a reference photocell for comparison, and sampling by electronic means rejecting spurious signals, with control to respond with a detection signal to user-specified light transmission increased or decreased by the sample and/or molecular marker.

U.S. Pat. No. 5,104,512 issued to Gombocz et al. discloses an electrophoretic system which allows for carrying out electrophoresis while monitoring and regulating the temperature and the electrical field gradient in the gel. In addition, photometric monitoring is provided so as to monitor the progress of the electrophoretic separation and vary conditions to change the progress as desired. A computer is employed which receives the signals from the electrophoretic and photometric apparatuses and regulates temperature and voltage to either maintain conditions, or change the conditions to vary the progress of the electrophoresis. Gel molds are provided for forming the lanes in a gel plate, as well as a light module, for reading the bands present in the gel lanes with the photometer.

U.S. Pat. No. 5,268,568 issued to Lee discloses a device for detecting a marker dye band which is used to monitor the progression of biological macromolecules in gel electrophoresis. The device mounts external to the gel box, and utilizes a single light detector and a pair of AC activated light sources. The light sources produce reflected or transmitted light signals which, when balanced at the detector, cancel. When the marker dye is absent the light signals are balanced, and no signal is detected. When the marker dye is present at a specific detection point within the gel, the light reflected (or transmitted) is no longer balanced and a signal is detected.

U.S. Pat. No. 7,967,968 issued to Kober et al. discloses a method and system for use in analyzing a sample. The method comprises applying real time monitoring to a sample while undergoing a separation process consisting of spatial separation of molecules of different molecular weights in the sample. The system includes a monitoring unit configured to be integrated with a separation unit in which the separation process takes place.

U.S. Pat. No. 6,068,753, issued to Sarrine et al. discloses an apparatus for electrophoresing a sample and for thereafter either scanning in the visible mode or the fluorescent mode, under control of a central processor, to provide scanning densitometry of the electrophoresed sample, and with the fluorescent mode scanning being performed in situ. The apparatus includes a gantry which moves from left to right in the XY plane. The gantry draws, delivers and deposits the samples and reagents, and includes safety devices to prevent the gantry from movement and damage when there are obstructions in the path of the gantry. A fluorescent scanning unit is moved by X- and Y-direction motors to position a photomultiplier over an electrophoresed sample. In this way, the electrophoretic sample can remain fixed in place during sample delivery, ultraviolet exposure and measurement operations.

There is a need for further electrophoresis controllers and electrophoresis apparatus employing the same.

SUMMARY OF THE INVENTION

In a first aspect, the present disclosure provides an electrophoresis controller for use with an electrophoresis apparatus having a gel matrix disposed between electrodes for separation of particles along with a tracking dye. The electrophoresis controller includes a sensor system and a controller. The sensor system includes a support, a light emitter, and a light receiver. The support includes a first portion positionable on a first side of the gel matrix and a second portion positionable adjacent a second side of the gel matrix. The light emitter is positioned on the first portion of the support for emitting light onto one side of the gel matrix. The light receiver is positioned on the second portion of the support adjacent to the other side of the gel matrix for receiving light from the light source passing through the gel matrix. At least one of the light emitter and the light receiver includes a light guide having a first end and a second end. The first end is positioned on the support and facing the gel matrix, and the second end is positioned remote from the sensor system. The controller is operably connected to the sensor system for monitoring a change in the light from the illuminated gel matrix due to migration of the tracking dye into the illuminated gel matrix and received by the light receiver.

In a second aspect, the present disclosure provides an electrophoresis controller for use with an electrophoresis apparatus having a gel matrix disposed between electrodes for separation of particles along with a tracking dye. The electrophoresis controller includes a sensor system, a light detector, and a controller. The sensor system includes a support, a light source, and a light guide. The support includes a first portion positionable on a first side of the gel matrix and a second portion positionable adjacent a second side of the gel matrix. The light source is positioned on the first portion of the support for emitting light onto one side of the gel matrix. The light guide includes a first end and a second end. The first end is positioned on the second portion of the support adjacent to the other side of the gel matrix for receiving light from the light source passing through the gel matrix. The light detector is operable for receiving light from the second end of the light guide for detecting light from the illuminated gel matrix. The controller is operably connected to the light detector for monitoring a change in the light from the gel matrix due to migration of the tracking dye into the illuminated gel matrix.

In a third aspect, the present disclosure provides an electrophoresis controller for use with an electrophoresis apparatus having a gel matrix disposed between electrodes for separation of particles along with a tracking dye. The electrophoresis controller includes a sensor system, a light source, a light detector, and a controller. The sensor system includes a support having a first portion positionable on a first side of the gel matrix and a second portion positionable adjacent a second side of the gel matrix, a first light guide having a first end and a second end, the first end positioned on the first portion of the support adjacent to the first side of the gel matrix for emitting light onto the gel matrix, and a second light guide having a first end and a second end, the first end positioned on the second portion of the support adjacent to the other side of the gel matrix for receiving light from the light source passing through the gel matrix. The light source is operable for emitting light into the second end of the first light guide. The a light detector is operable for receiving light from the second end of the light guide for detecting light from the illuminated gel matrix. The controller is operably connected to the light detector for monitoring a change in the light from the gel matrix due to migration of the tracking dye into the illuminated gel matrix.

In a fourth aspect, the present disclosure provides an electrophoresis controller for use with an electrophoresis apparatus having a gel matrix disposed between electrodes for separation of particles along with a tracking dye. The electrophoresis controller includes a sensor system, a light source, and a controller. The sensor system includes a support having a first portion positionable on a first side of the gel matrix and a second portion positionable adjacent a second side of the gel matrix, a light guide having a first end and a second end, the first end positioned on the first portion of the support adjacent to the first side of the gel matrix for emitting light onto the gel matrix, and a light detector positioned on the second portion of the support adjacent to the other side of the gel matrix for receiving light from the light source and passing through the gel matrix. The light source is operable for emitting light into the second end of the light guide. The controller is operably connected to the light detector for monitoring a change in the light from the gel matrix due to migration of the tracking dye into the illuminated gel matrix.

In a fifth aspect, the present disclosure provides an electrophoresis controller for use with an electrophoresis apparatus having a gel matrix disposed between electrodes for separation of particles along with a tracking dye. The electrophoresis controller includes a sensor system having a support having a first portion positionable on a first side of the gel matrix and a second portion positionable adjacent a second side of the gel matrix, a first light emitting diode is positioned on the first portion of the support adjacent to the first side of the gel matrix for emitting light onto the gel matrix, and a second light emitting diode is employed as a photodetector positioned on the second portion of the support adjacent to the other side of the gel matrix for receiving light from the first light emitting diode and passing through the gel matrix.

In a sixth aspect, the present disclosure provides a sensor system for use with an electrophoresis apparatus having a gel matrix disposed between electrodes for separation of particles along with a tracking dye. The sensor system includes a support having a first portion positionable on a first side of the gel matrix and a second portion positionable adjacent a second side of the gel matrix, a light emitter positioned on the first portion of the support for emitting light onto one side of the gel matrix, and a light receiver positioned on the second portion of the support adjacent to the other side of the gel matrix for receiving light from the light source passing through the gel matrix. At least one of the light emitter and the light receiver includes a fiber optic cable having a first end and a second end, the first end being positioned on the support and facing the gel matrix, and the second end being remote from the sensor system.

In a seventh aspect, the present disclosure provides a method for controlling an electrophoresis apparatus having a gel matrix disposed between electrodes for separation of particles along with a tracking dye. The method includes emitting a beam of light from the light emitter onto a first side of the gel matrix to illuminate a portion of the gel matrix, receiving light from the illuminated gel matrix in a light receiver, and monitoring a change in the light from the illuminated gel matrix due to migration of the tracking dye into the illuminated gel matrix and received by the light receiver. At least one of the light emitter and the light receiver including a light guide having a first end and a second end. The first end of the light guide is disposed adjacent to the gel matrix and the second end of the light guide is disposed remotely from the gel matrix.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

FIG. 2 is an enlarged view of the sensor of the electrophoresis controller of FIG. 1;

FIG. 3 is a cross-sectional view of the sensor of FIG. 2;

FIG. 4 is a cross-sectional view of an alternative embodiment of a sensor in accordance with aspects of the present disclosure;

DETAILED DESCRIPTION OF THE INVENTION

The present disclosure, in various aspects, may generally include an electrophoresis dye sensor and/or controller that can be used to indicate the end of electrophoresis experiments and shut off the power source and alert the end user via an audio, visual, telephone message, phone call, and/or text message. For example, tracking dyes are often used as the analytes being separated are mostly colorless, and their progress through the gel during electrophoresis cannot easily be followed visually. Anionic tracking dyes of known electrophoretic mobility are usually added alongside the sample being analyzed. These dyes are colored under the experimental conditions and their negative charge causes them to move towards the anode over the course of the experiment. An electrophoresis dye sensor or controller may be operable for detecting the dye front as it moves through an electrophoresis system. When the dye front is detected, the power supply to the system may be shut off, thereby terminating the electrophoretic separation of the sample. Dye detection is also accompanied by a signal, to alert the operator that the process is complete. Finally, the system may be portable, such that the system can be applied to multiple different electrophoresis systems and relocated throughout the laboratory as needed. The system may include several different elements or features such as automation, dye sensors, control of a power source, signals to the operator, and portability which together may define a portable device which senses the movement of non-fluorescent dyes through an electrophoresis system and automatically terminates the electric field applied to the electrophoresis system when the dye reaches a predetermined point.

In one embodiment of the present disclosure, an electrophoresis controller may be operable with existing conventional gel electrophoresis systems available on the market.

Gel systems currently available on the market can be divided into two main groups, Agarose or horizontal gel systems, and Polyacrylamide or vertical gel systems. The electrophoresis controller may be readily adapted to fit the wide range of existing systems. In addition, the electrophoresis controller may be incorporated into and be a part of an electrophoresis system as described in greater detail below.

Figure 1:
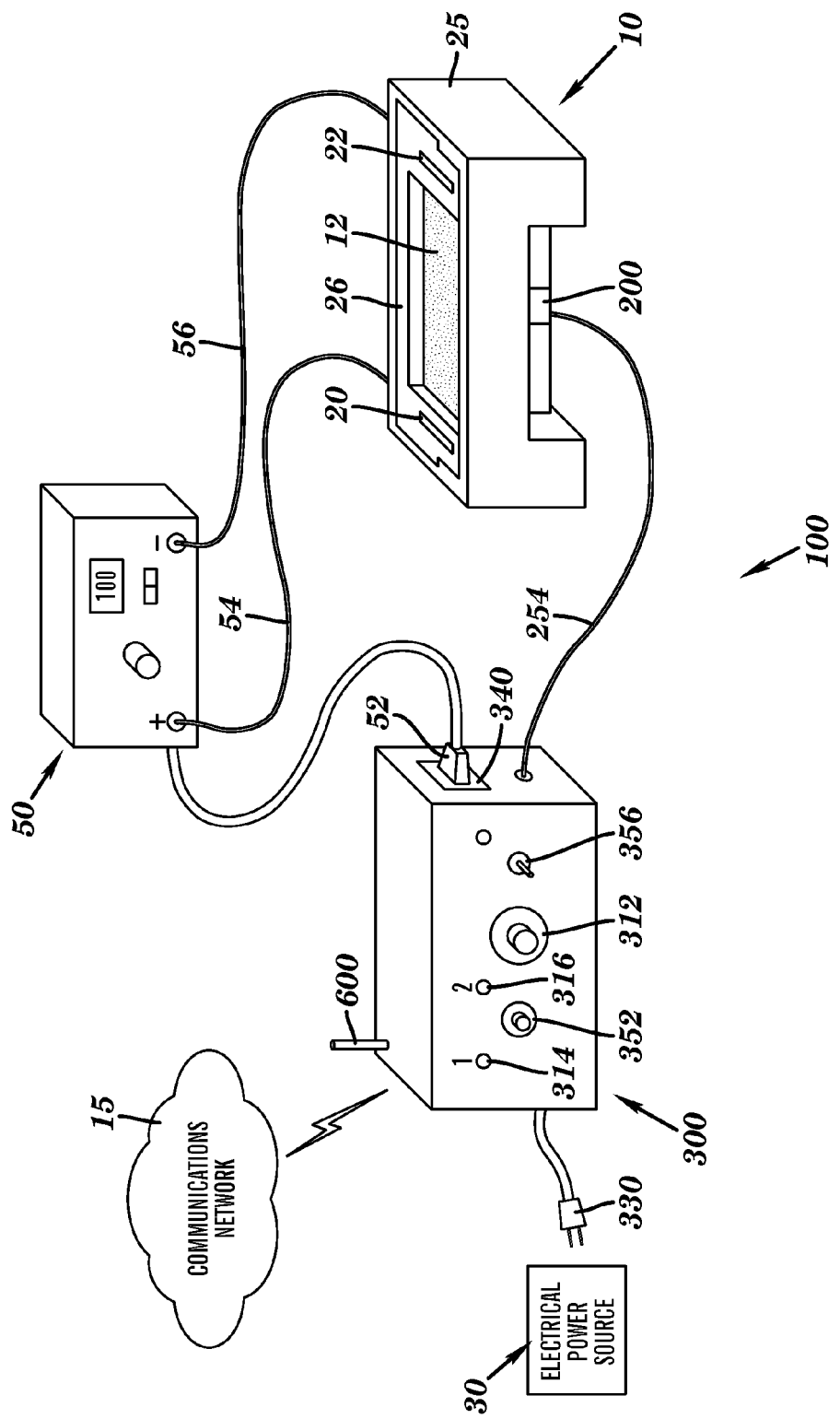
FIG. 1 is one embodiment of an electrophoresis controller in accordance with aspects of the present disclosure.

FIG. 1 illustrates one embodiment of an electrophoresis controller 100 in accordance with aspects of the present disclosure. Electrophoresis controller 100 is operably connectable to an electrophoresis apparatus 10 comprising a holder 25 for positioning a gel matrix 12 between electrodes 20 and 22 for separating particles using a tracking dye. In this exemplary embodiment, electrophoresis controller 100 may include a sensor 200 positionable adjacent to a gel matrix, a controller 300 connectable to an electrical power source 30 and to a power supply 50 for providing a voltage across the electrodes of the electrophoresis apparatus, and a transmitter 600 such as a wireless transmitter operably connectable to a communications network 15. Sensor 200 may be operably connected to controller 300 via a cable 254. As described in greater detail below, controller 300 is operable for turning off electrical power to power supply 50 based on a change in light from the illuminated gel matrix, such as light reflected from the illuminated gel, due to migration of the tracking dye into the illuminated gel matrix.

For example, controller 300 may include an electrical plug 330 electrically connectable to electrical power source 30 such as an outlet for receiving 120 volt alternating current (AC) for powering electrophoresis controller 100. Controller 300 may also have an electrical socket 340 electrically connectable to an electrical plug 52 of power supply 50 for providing 120 volt alternating current to power supply 50. Power supply 50 may be connected via wires 54 and 56 for providing direct current such as 1 volt to 100 volts direct current (DC) to electrodes 20 and 22, respectively of electrophoresis apparatus 10. Controller 300 is operable for turning off electrical power to power supply 50, and thus, turning off the supply of direct current to electrodes 20 and 22.

In one embodiment, sensor 200 is positionable under electrophoresis apparatus 10. As best shown in FIGS. 2 and 3, sensor 200 may include a housing 210, a light source 220 for emitting light into the gel matrix in the electrophoresis apparatus, and a first light detector 230 and a second light detector 240 disposed adjacent to the light source for detecting light from the light source reflected from the gel matrix. The light source and the light detectors may be disposed on a top surface of housing 210. The housing may be about 1.5 inches wide, 1.5 inches deep, and 1.5 inches high. The light source may be disposed between the two light detectors. The light detectors may be spaced about ¼ inch to about ½ inch away from the light source. The light source may emit a generally wide beam of light. Sensor 200 may include raised ridges 212 and 214 that allow for easy movement and also permit insulation by an air pocket in order to inhibit heating of the gel matrix by the light source. For example, the raised ridges may contact the lower surface of the electrophoresis apparatus. As shown in FIG. 4, in another embodiment, a sensor 260 may include a housing 261 defining cavities 265 having an opening 267 for receiving a generally narrow beam of light from the illuminated gel matrix. Such a configuration may increase the sensitivity of the light detector, sensor, and/or controller. The light detector may comprise a photodiode and the light source may comprise a light emitting diode.

Figure 5:
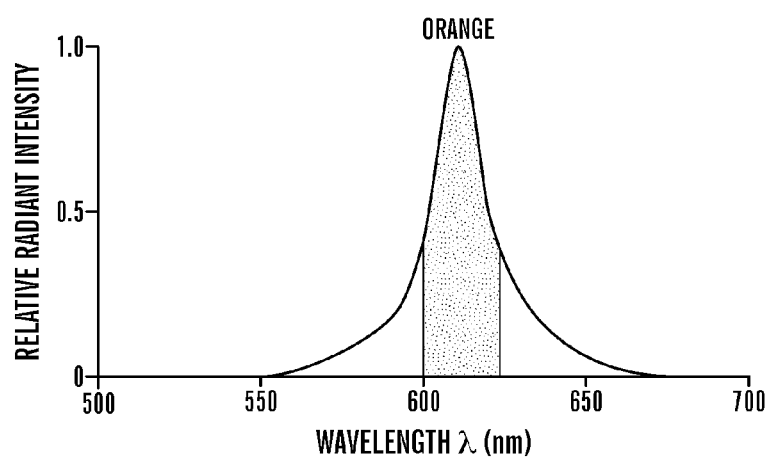
FIG. 5 is an emission spectrum of the light source of FIG. 2.
Figure 6:
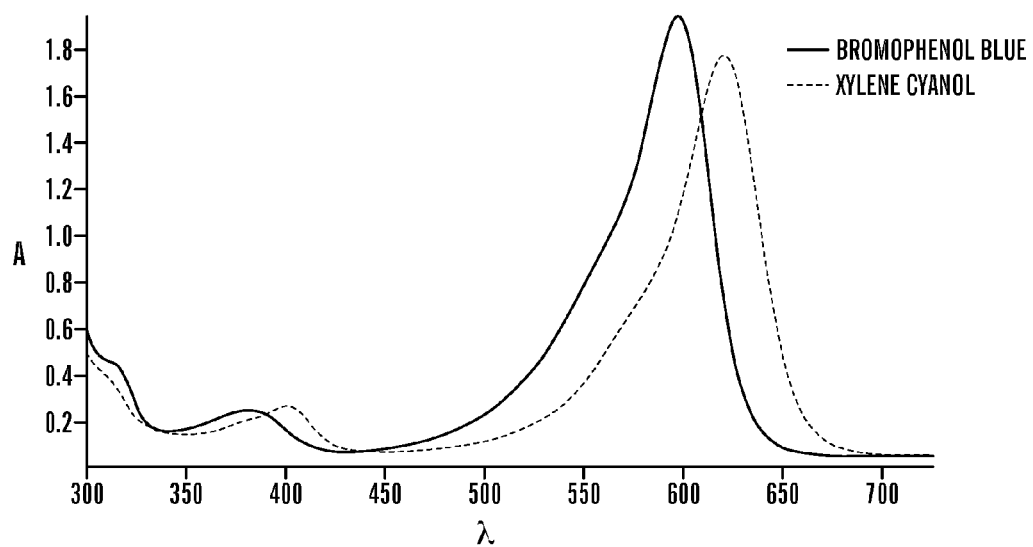
FIG. 6 is an absorption spectra of bromophenol blue and xylene cyanol, working concentration taken in a 1 mm 4% PAGE gel.

The light source such as a light emitting diode reduces, if not eliminates, the need for or dependence on ambient light for operation of the electrophoresis controller. In addition, an opaque cover may be placed over the electrophoresis apparatus during operation. Suitable photodiodes include photodiodes SFH213 (OSRAM-opto-Semiconductors, Northville, Mich.) and OP906 (Optec, Lowell, Mich.) which have high sensitivity, and a moderate size and shape making them suitable for a compact sensor design. Suitable LEDs include LEDs WP7113SEC/J4 and WP710A10SEC/J4 (KingBright, City of Industry, Calif.) which work well with the two typically used dyes, namely bromophenol blue and xylene cyanol. FIG. 5 illustrates the emission spectrum of LEDs WP7113SEC/J4 and WP710A10SEC/J4. The LEDs emit high intensity light of about 14000 mcd and about 10000 mcd, respectively, and provide consistent intense light that relatively reduces the contribution of ambient light. In one embodiment, it may be desirable to remove the lens or a portion of the lens of the LED so that the light emitted extends over a wider or broader range. In addition, the emission spectra of the LEDs exhibit good overlap with the absorption maxima of the two dyes, providing increased sensitivity, as shown in FIGS. 5 and 6.

With reference again to FIGS. 2-4, the LED and the photodiodes may be assembled in a compact unit depicted. The LED and two photodiodes may be arranged in series with respect to the path of the migrating dye. One photodiode may act as a reference to compensate for ambient light and the other as a detector of the migrating dye. Interference due to ambient light may be inhibited by a) utilizing two photodiodes, one as a dye sensor and the other as a reference to compensate for ambient light interference, b) optimizing the depth at which the photodiodes are set in the housing block so that only a narrow beam of light is able to reach the photodiodes, and c) utilizing an LED with an emission maximum that has a good overlap with the absorption maxima of the two dyes.

Figure 7:
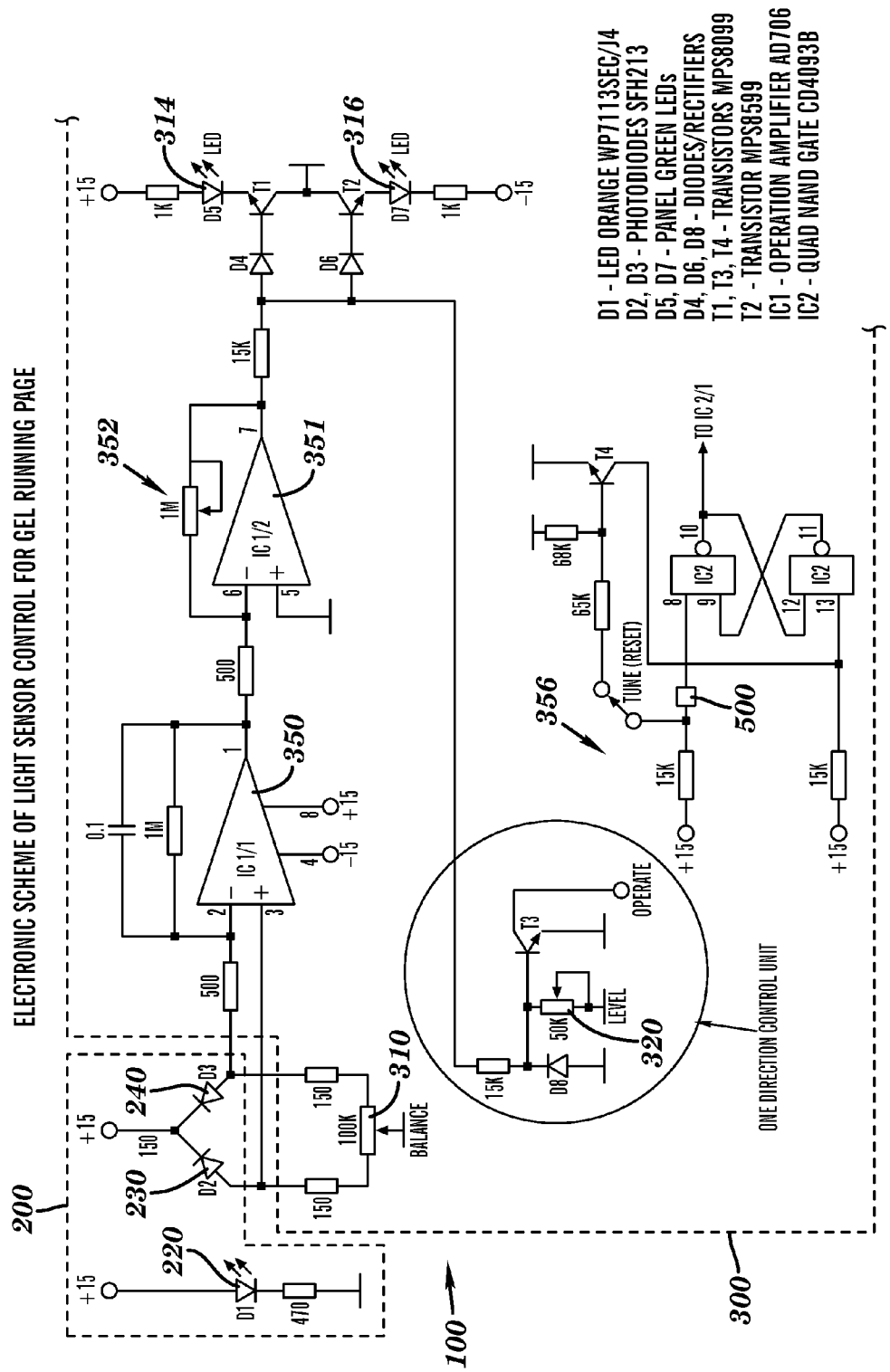
FIGS. 7 and 8 are schematic illustrations of one embodiment of the controller of FIG. 1.
Figure 8:
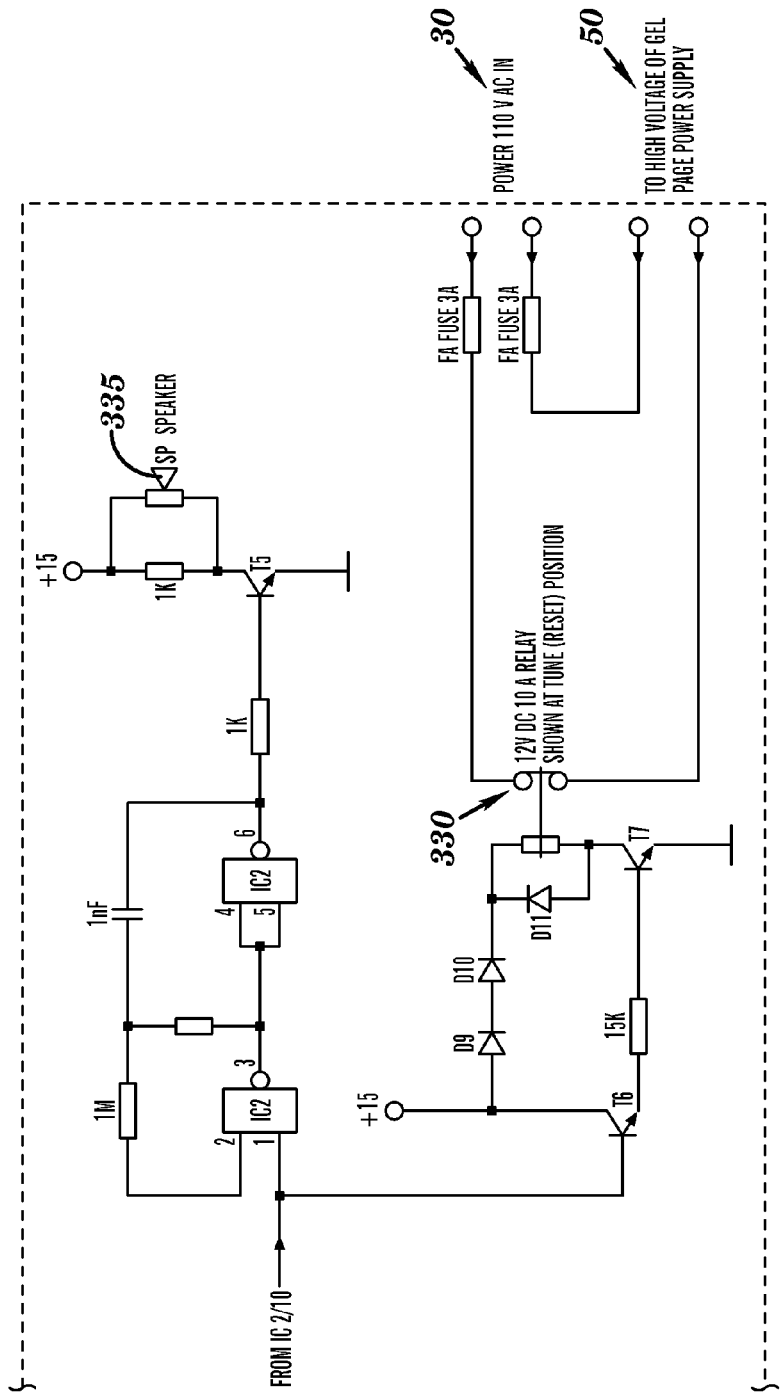

FIGS. 7 and 8 are schematic illustrations of one embodiment of controller 100. For example, sensor 200 may include light source 220 and light detectors 230 and 240. Controller 300 may include a variable resistor 310 (adjustable by knob 312 as shown in FIG. 1) for balancing light detectors 230 and 240, which balancing may be observed by an operator via visual indicators 314 and 316 (such as LEDs 314 and 316 disposed on the front of controller 300 as shown in FIG. 1). Sensitivity may be adjusted by variable resistors 320 and 352. Controller 300 may be operable to activate a switch 330 to turn off electrical power to power supply 50, and activate a speaker 335. The balancing capability of the controller allows for compensating for ambient light and adjusting the system to optimize the sensitivity mode, e.g., take into account different sensitivity of photoelectric sensors.

Two signals from photodiodes or light detectors 230 and 240 are received by operational amplifier 350 which has a gain of about 2,000. The signal output from this amplifier goes to the next amplifier 351 which has a negative feedback with a variable resistor 352 of 1 Mega Ohm. This resistor provides a variable gain of this amplifier. The sensitivity of the controller can be adjusted by varying the gain of the amplifier 351 to fit experimental needs. Signal from amplifier 351 activates audible alarm 335 and shutting off relay 330. The signals to speaker 335 and relay 330 are controlled by leveler 320 which sets the threshold to activate the audible alarm and shut off the relay. In addition, a visual alarm or light may be provided.

Figure 9:
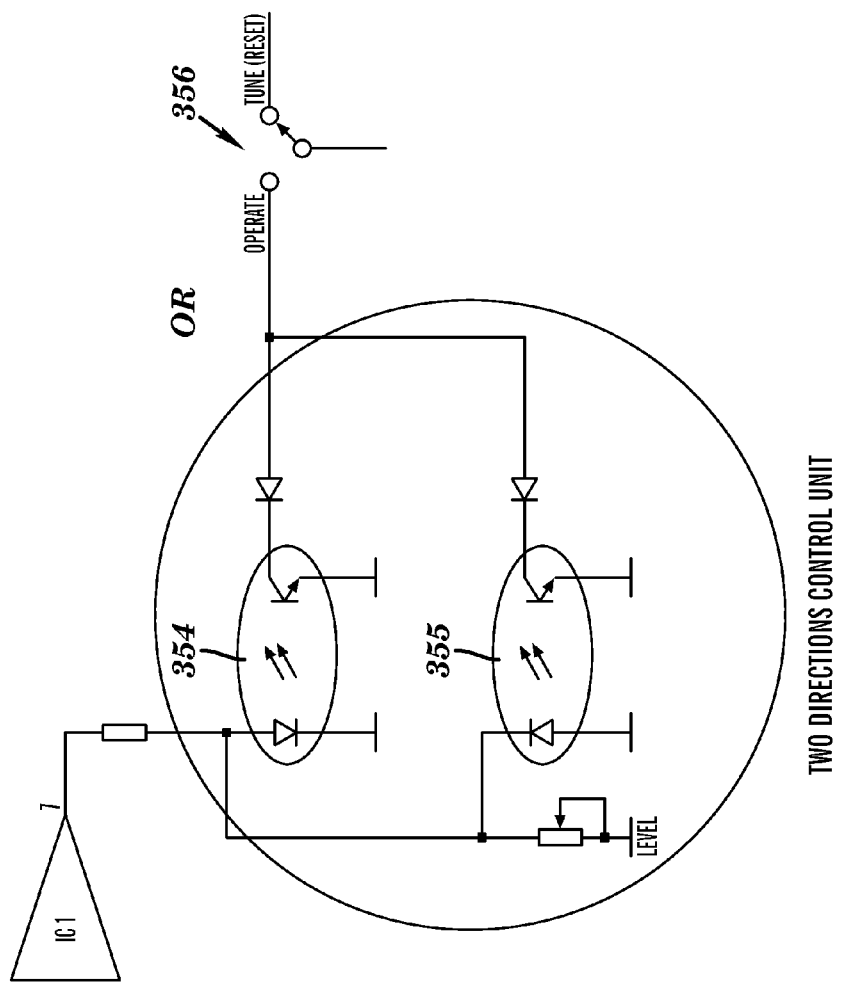
FIG. 9 is a schematic illustration of an alternative embodiment of a logical OR sensing for use in the controller in accordance with aspects of the present disclosure.

FIG. 9 is a schematic illustration of an alternative embodiment of a logical OR sensing for use in the controller. In this case, output signal from amplifier 351 activates one of the two optical couplers 354 and 355 depending on the polarity of the output signal. The output of the optical couplers opens or closes logic gate 356. This allows the system to trigger the alarm when the dye reaches any one of the two photosensors.

Figure 10:
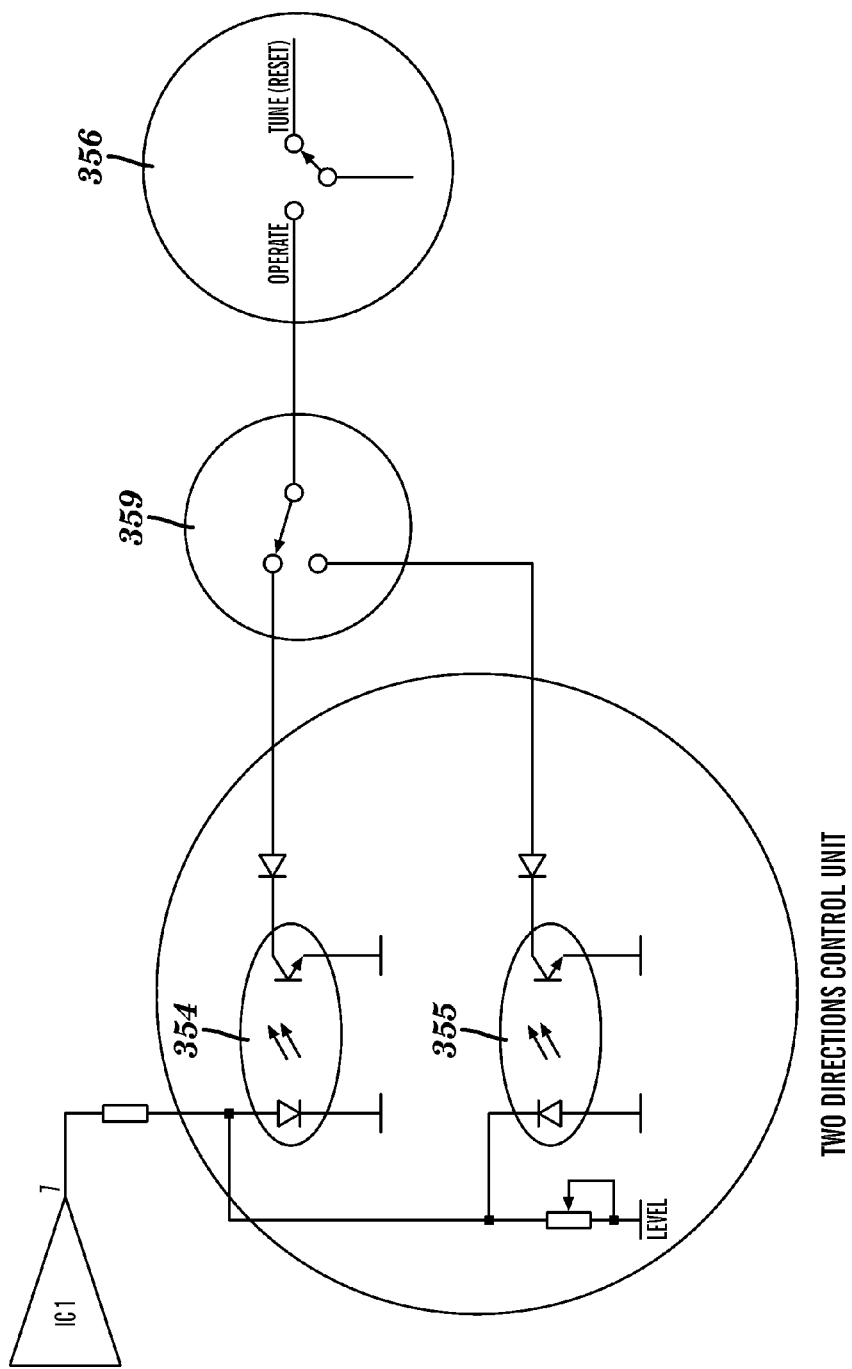
FIG. 10 is a schematic illustration of an alternative embodiment of a bi-directional sensing for use in a controller in accordance with aspects of the present disclosure.

FIG. 10 is a schematic illustration of an alternative embodiment of a bi-directional sensing for use in the controller. The output of each optical coupler opens or closes logic gate 356 depending on the position of a direction switcher 359. The directional switcher allows each photodiode to switch roles from "dye sensing photodiode" to "ambient light compensator" and vice versa.

Figure 11:
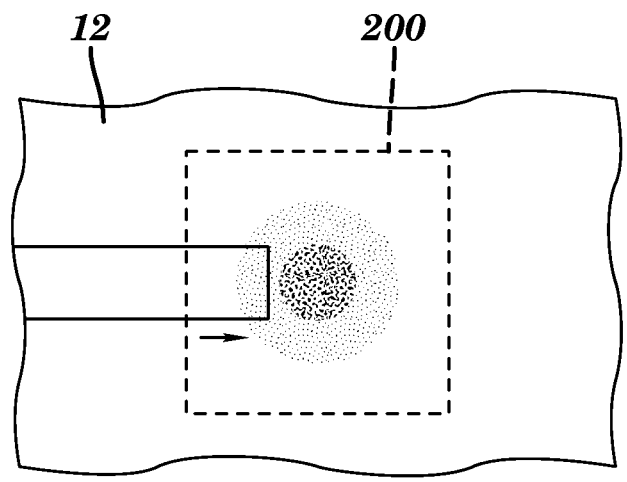
FIGS. 11 and 12 are top views of a portion of the gel matrix in which a portion of the gel matrix is illuminated by the light source of FIG. 2.
Figure 12:
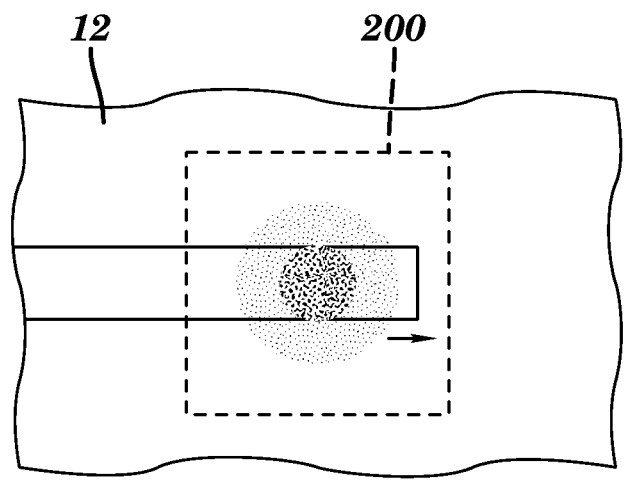

FIG. 11 is a top view of a portion of the gel matrix with the sensor disposed below the gel matrix and illustrating a portion of the gel matrix illuminated by the light source. For example, with reference to the logical OR sensing of FIG. 9, controller 300 (FIG. 1) may be configured to turn off the power supply upon detection by a first one of the light detectors receiving a reduced amount of light due to the dye moving across the illuminated portion of the gel. In another configuration, as shown in FIG. 12, controller 300 (FIG. 1) may be configured to turn off the power supply upon detection by both the light detectors receiving a reduced amount of light due to the dye moving across the illuminated portion of the gel. This configuration allows using generally the entire length of the gel matrix as the sensor can be placed adjacent to the end of the gel matrix.

Figure 13:
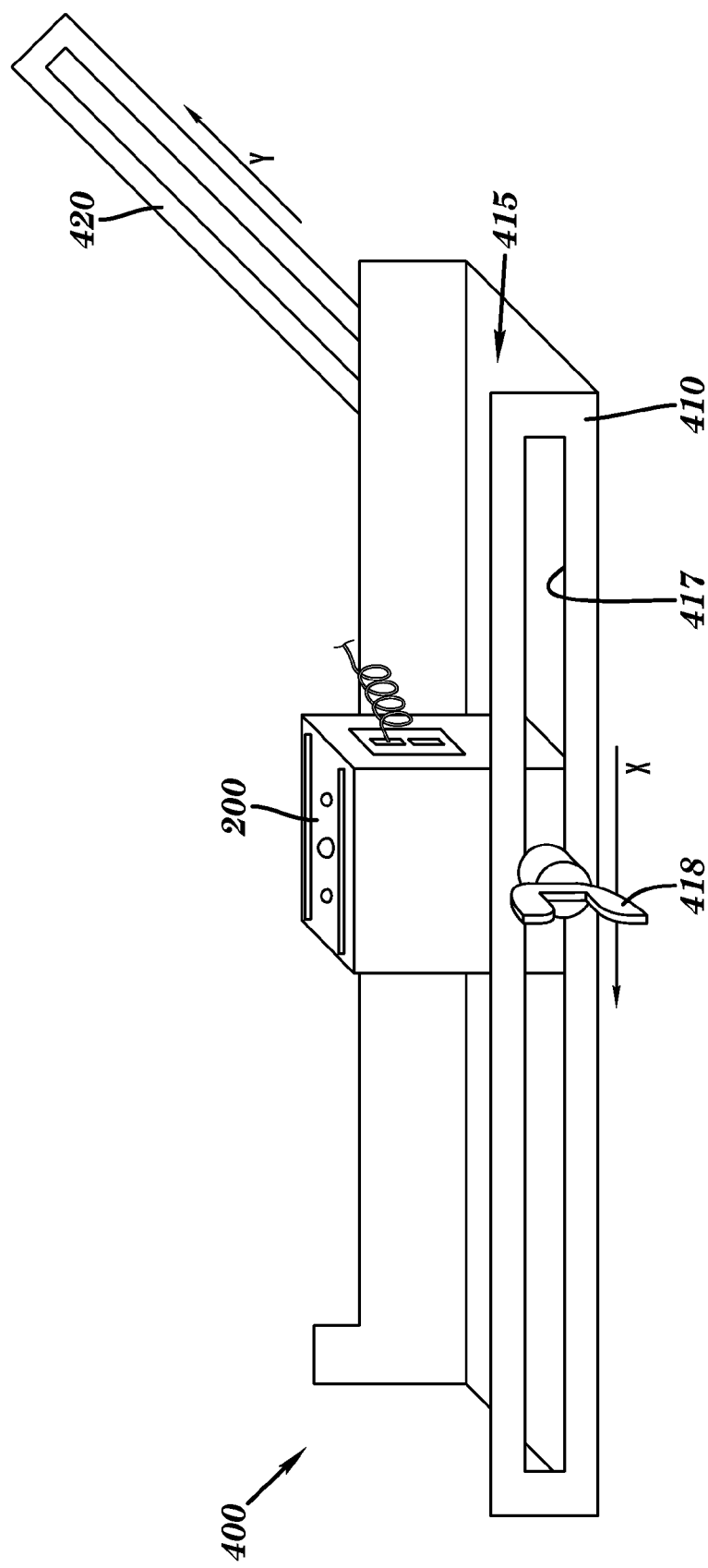
FIG. 13 is a perspective view of a support attachable to the sensor and to the electrophoresis apparatus of FIG. 1 for supporting the sensor adjacent to a gel matrix.

FIG. 13 illustrates a support 400 attachable to sensor 200 and electrophoresis apparatus 10 (FIG. 1) for supporting the sensor adjacent to the gel matrix. For example, support 400 may have side walls 410 having an elongated channel 415 therein to allow sensor 200 to be movably positionable along the length of support 400, and thus the length of the gel matrix. An elongated aperture 417 disposed in one of the side wall may allow the sensor to be fixedly retained in place with a clamp or thumb screw 418. A second support 420 may be provided for allowing support 400 to move along the width of the electrophoresis apparatus, and thus, the width of the gel matrix. Accordingly, desirably any position or location of the gel matrix may be monitored.

The support or XY mounting stage may be constructed from Plexiglas. The sensor fits into the stage trough and can be tightened into place. The whole assembly can be moved in either the x or y direction to adjust the position of the sensor. The stage has two guide rails that allow for easy alignment of the sensor in the path of the migrating dye. It will be appreciated that similar designs can also be applied to other gel electrophoresis systems.

Figure 14:
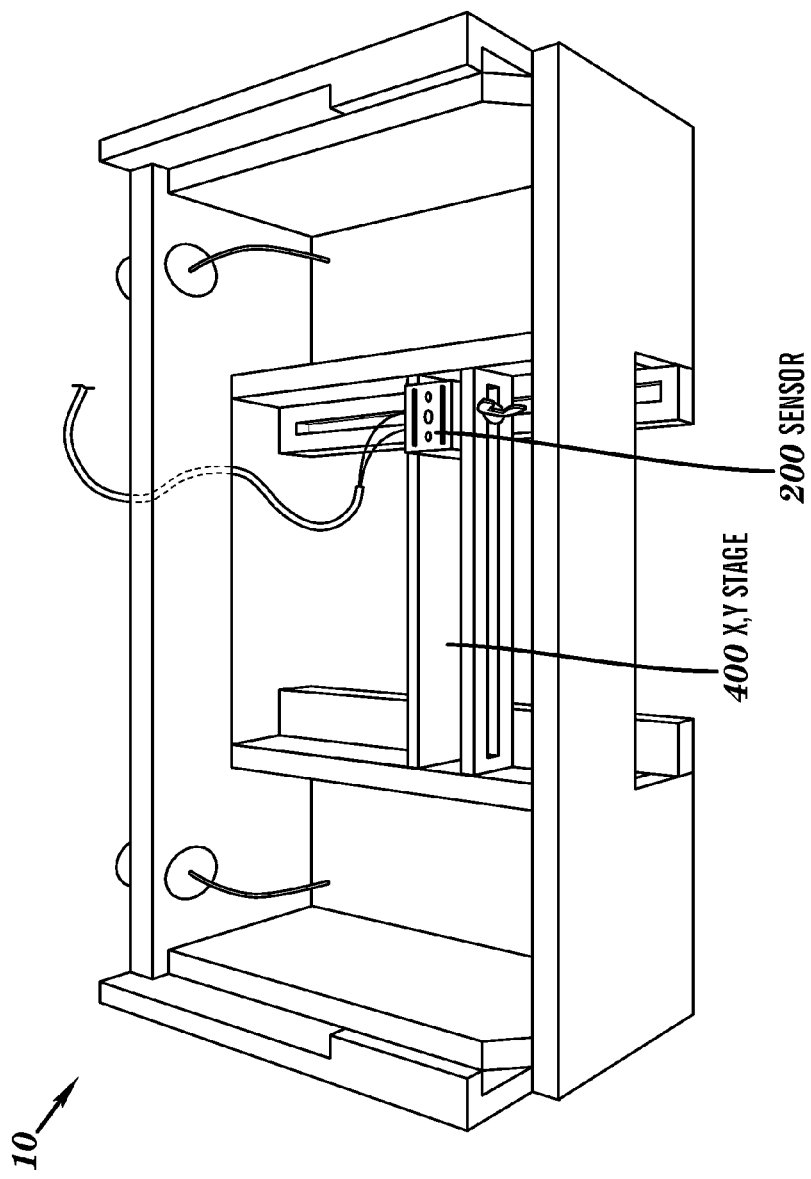
FIG. 14 is a top perspective view of the electrophoresis apparatus and sensor of FIG. 1.

FIG. 14 is an enlarged top perspective view of electrophoresis apparatus 10, sensor 200, and support 400.

With reference again to FIG. 7, controller 100 may include a delay system 500 in accordance with aspects of the present disclosure. Delay system 500 avoids false triggering of the alarm system (e.g., turning off the power supply and activating the alarm due to detection by the sensor of moving shadows at high sensitivity settings). For example, the shadow of an operator checking on a gel may turn off the power supply and activate the alarm due to the presence of generally strong ambient lighting. The delay system incorporated into the controller may be operable so that only signals that persist for greater than a time of about ½ minute turns off the power supply and/or triggers an alarm.

Figure 15:
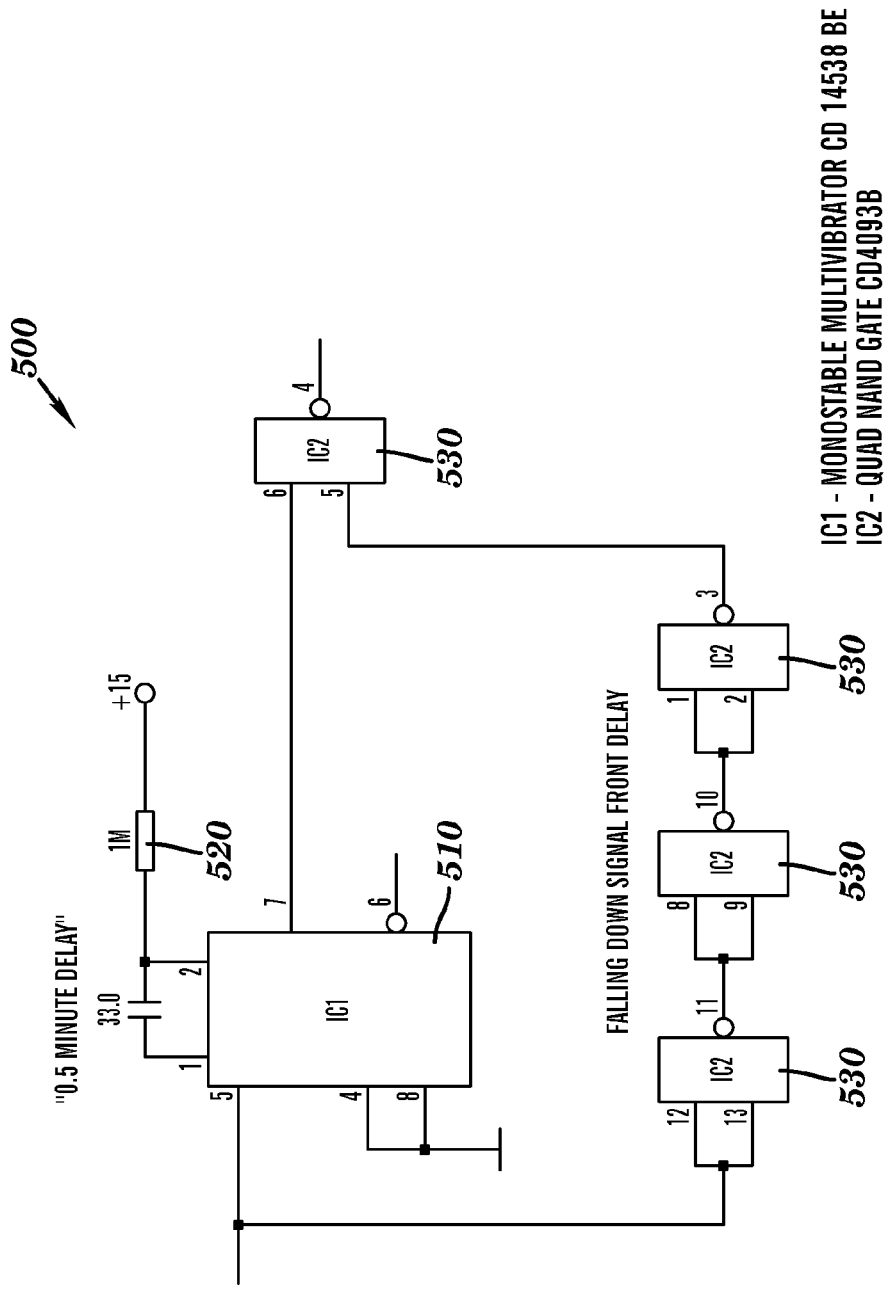
FIG. 15 is a schematic illustration of a delay circuit for use in the controller of FIG. 1.

With reference to FIG. 15, delay system 500 may include a monostable multivibrator 510, a resistor 520 for setting the time delay, and quad NAND gates 530. The monostable multivibrator has one state which is stable, and the other state is unstable (transient). A trigger pulse causes the circuit to enter the unstable state. During this period of time gate 530 is closed that makes triggering the alarm system impossible. After entering the unstable state, the circuit will return to the stable state after a set time. Such a circuit creates a timing period of fixed duration. It will be appreciated that other suitable delay systems may be employed.

With reference again to FIG. 1, another aspect of the present disclosure is directed to a lid 26 for covering the electrophoresis apparatus. For example, a suitable lid may avoid false activation of the alarm system due to detection by the sensor of light passing through condensation formed on the lid. For example, operation of the electrophoresis apparatus at maximum voltage for an extended period of time tends to from water droplets on the bottom side of the lid. The droplets may act as micro lenses, focusing light into the photodiode and giving rise to false alarm signals. Various lids may be employed to avoid such effects of condensation. One approach includes limiting entry of ambient light into the gel box by using a colored film or diffusing the light by utilizing different textured lids. For example, the lid may comprise a clear PLEXIGLASS acrylic sheet covered with red film. It was found that such a configuration was operable at very low sensitivities, and with high concentration of dye, e.g., 6 times working concentration. Another example includes the lid comprising a clear prism acrylic sheet in which the condensation agglomerates or gathers into large flat beads of about 2 cm in diameter. The large grouping of water had minimal curvature, even at its edges, which reduces the amount or light that was diffracted. Thus, the amount of ambient light entering the system remained unchanged as condensation formed. It is also appreciated that by operating the electrophoresis apparatus with the applied voltage to the gel at about 100 volts instead of a maximum 150 volts, lowering the sensitivity of the sensor, and increasing the concentration of dye to 4 times the typical working concentration, reduced and eliminated the problems associated with condensation.

Figure 16:
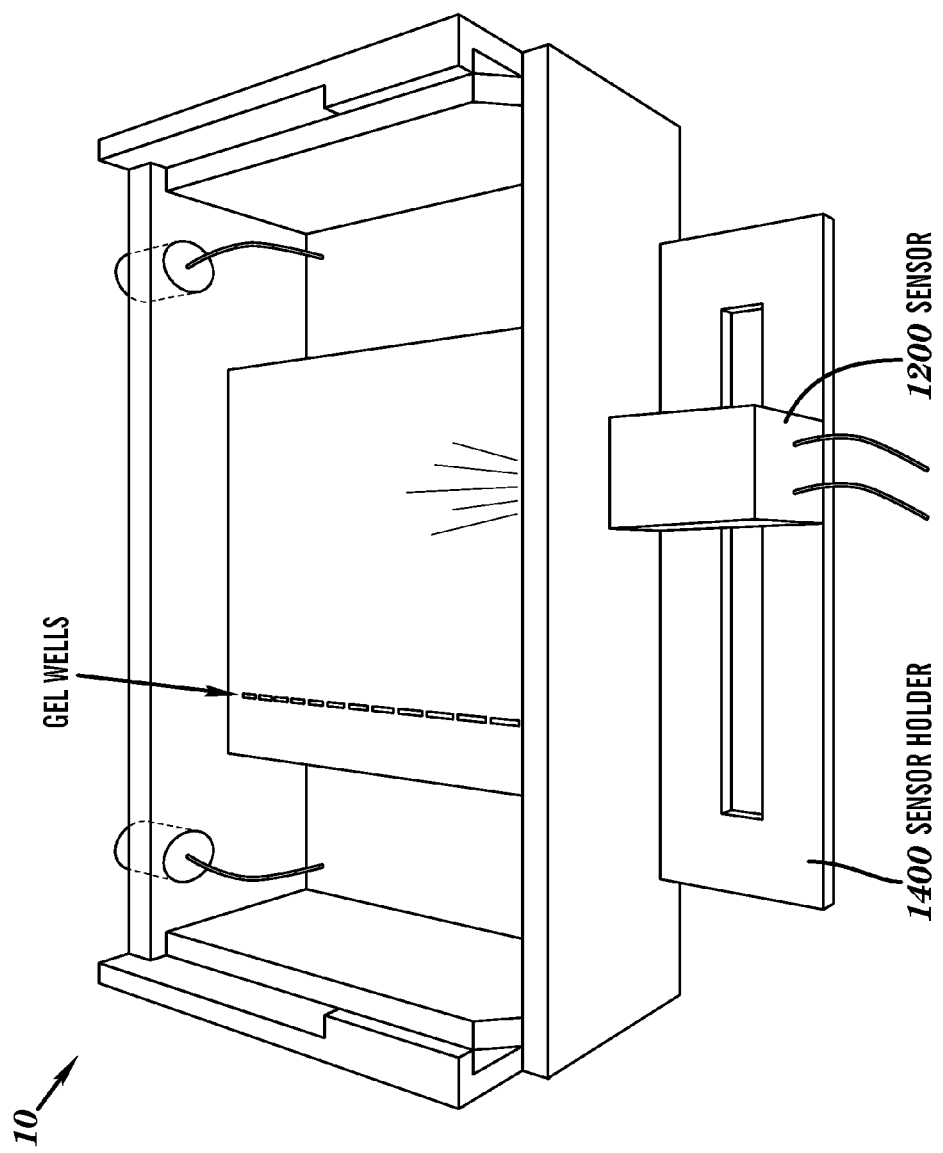
FIGS. 16 and 17 are top perspective views of another embodiment of a support for supporting a sensor adjacent to an electrophoresis apparatus in accordance with aspects of the present disclosure.
Figure 17:
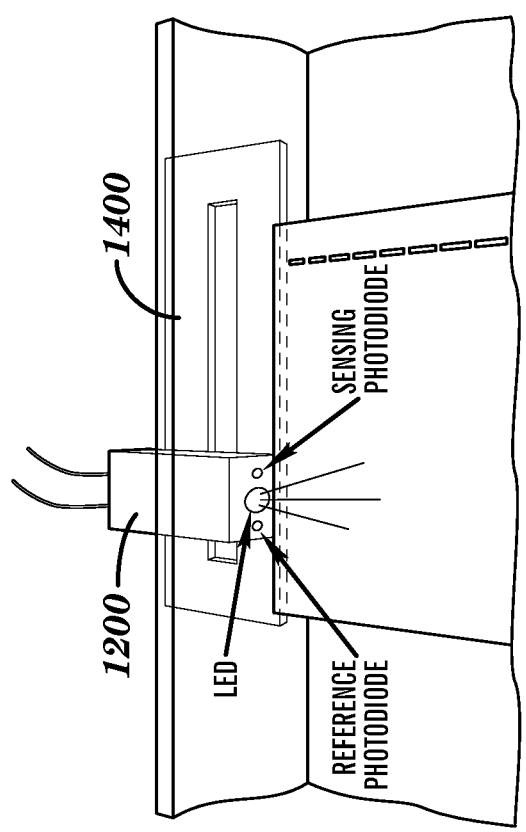

FIGS. 16 and 17 illustrate another embodiment of a support 1400 for supporting a sensor 1200 in accordance with aspects of the present disclosure adjacent to the side of the gel matrix. In this embodiment, the controller may be similar to the controller described above, and operably connected to sensor 1200 and to a power supply for use with existing electrophoresis apparatus 10. Support 1400 may be operably attachable to the side of electrophoresis apparatus 10.

By positioning the sensor along the edge of the gel matrix, the problems associated with the effects of condensation on the lid may also be avoided. In this embodiment, the lens curvature of the sensor of the LED was modified to widen the aperture of the irradiated light from about 20 degrees to about 30 degrees. In addition, the collimators of the photodiodes may be optimized to allow for improved sensitivity while reducing the entry of scattered ambient light. In this configuration, the sensor is operable to monitor the tracking dye disposed in the well position adjacent to the edge of the gel matrix. Desirably, a tracking dye selected for the first well is chosen having a faster mobility or the same mobility compared to the dyes selected for the remaining well in the gel matrix.

Figure 18:
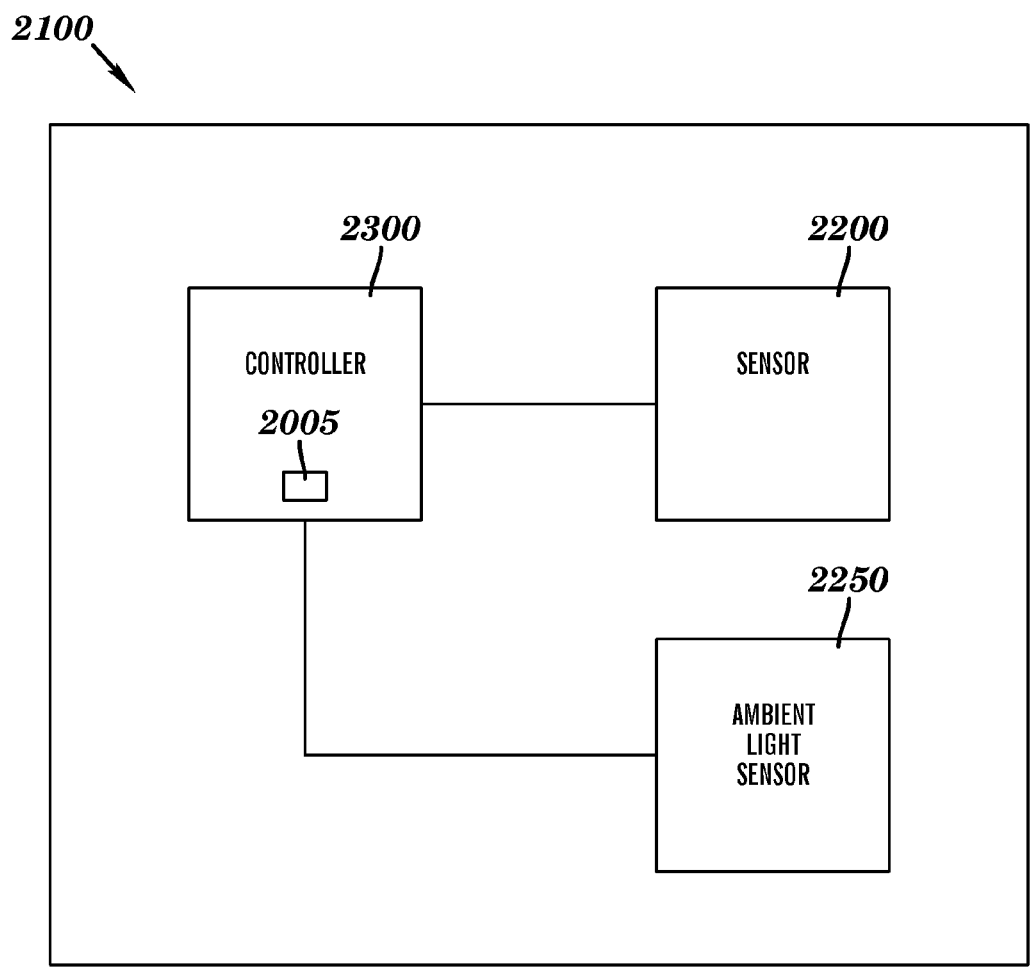
FIG. 18 is a block diagram of another embodiment of an electrophoresis controller in accordance with aspects of the present disclosure.

FIG. 18 illustrates a block diagram of another embodiment of an electrophoresis controller 2100 in accordance with aspects of the present disclosure. Electrophoresis controller 2100 is operably connectable to an electrophoresis apparatus for positioning a gel matrix between electrodes for separating particles using a tracking dye. In this exemplary embodiment, electrophoresis controller 2100 may include a sensor 2200 positionable adjacent to a gel matrix, and a controller 2300 connectable to an electrical power source and to a power supply for providing a voltage across the electrodes of the electrophoresis apparatus. Sensor 2200 may be similar to the sensors described above having a light source and two light detectors and may be operably connected to controller via a suitable cable. Controller 2300 is operable for turning off electrical power to the power supply based on a change in light from the illuminated gel matrix, such as light reflected from the illuminated gel, due to migration of the tracking dye into the illuminated gel matrix.

Figure 19:
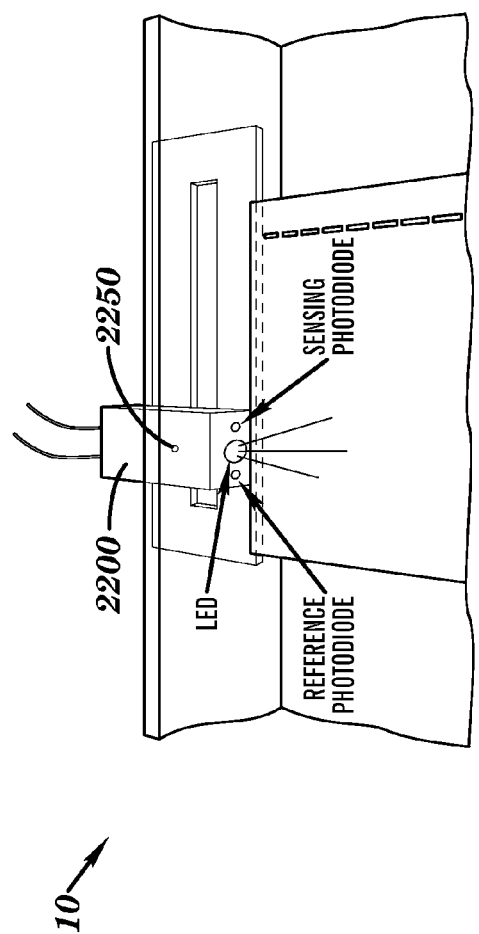
FIG. 19 is a top perspective view of the sensor and ambient light sensor of FIG. 18 disposed on a support attached to an electrophoresis apparatus.

Electrophoresis controller 2100 may also include an additional sensor such as an ambient light sensor 2250. Ambient light sensor 2250 or a third photodiode designated as a "searching" photodiode may be placed, for example, on top of or part of a sensor 2200, such as shown in FIG. 19, in order to access maximum ambient light and report any changes in ambient light. It will be appreciated that the ambient light sensor may be disposed at other suitable locations. From the present description, it will be appreciated that the use of an ambient light sensor may reduce and/or avoid the problems associated with modern laboratories that typically have motion sensor activated lights that turn the lights off and on depending on the activity in the laboratory, or where the electrophoresis system is located near a window wherein varying amounts of sunlight may generate a false alarm signal.

With reference again to FIG. 18, a microprocessor 2005 may be utilized to control and modulate the signals received by each photodiode and determine when the alarm will be triggered. The microprocessor may be utilized to automatically balance the controller or system before each run and eliminate the need for a user to manually balance the controller or system. The microprocessor may also be operably programmed to balance the system, control the various detectors, and determine when to signal the alarm.

Figure 20:
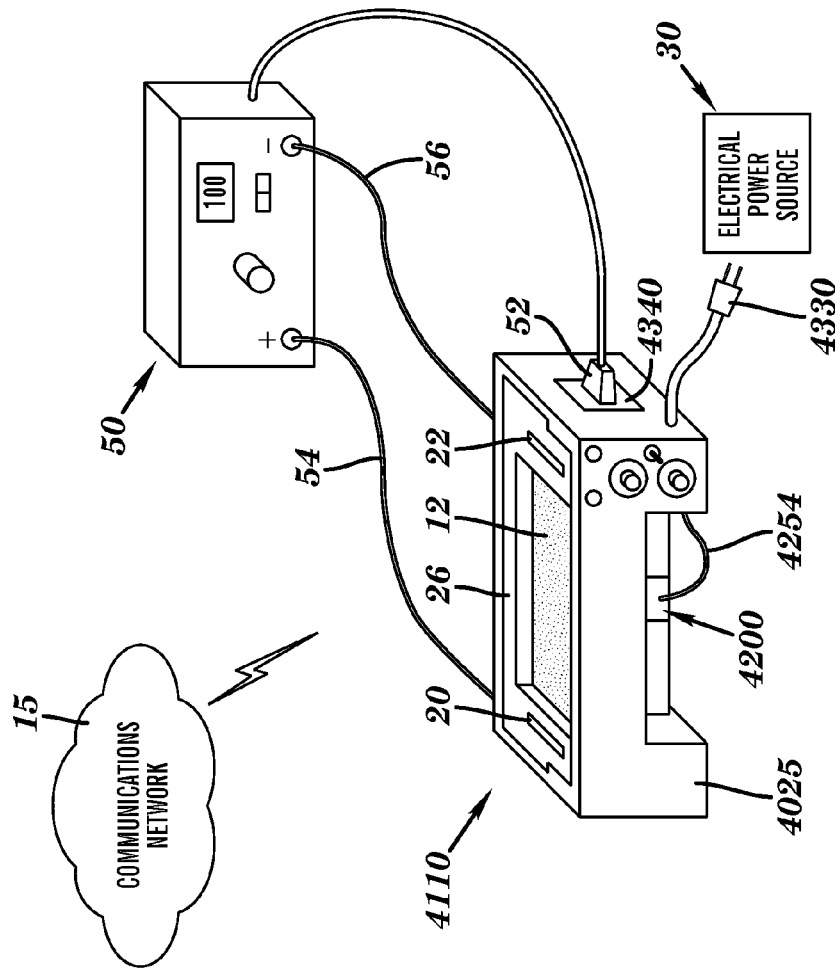
FIG. 20 is another embodiment of an electrophoresis controller in accordance with aspects of the present disclosure.
Figure 21:
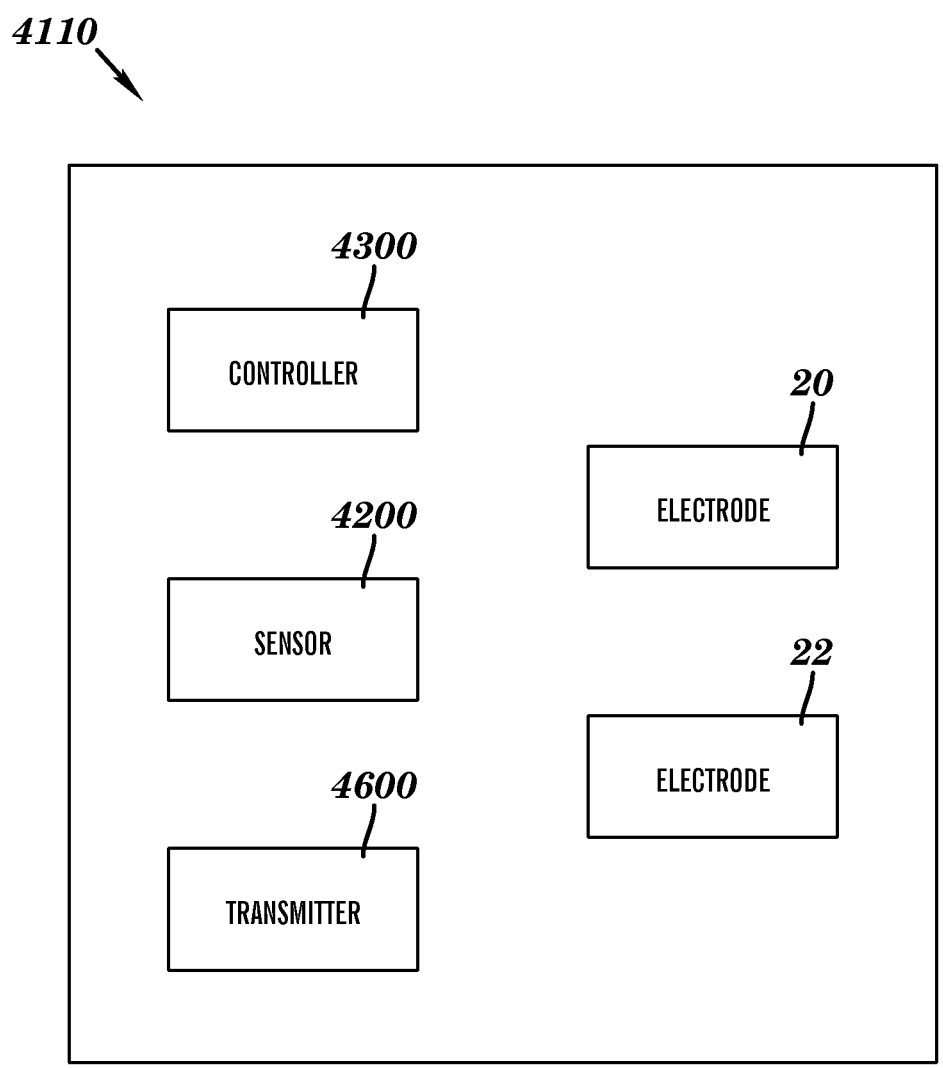
FIG. 21 is a block diagram of the electrophoresis controller of FIG. 20.

FIGS. 20 and 21 illustrate an embodiment of an electrophoresis apparatus 4110 in accordance with aspects of the present disclosure. Electrophoresis apparatus 4110, for example, may comprise a housing which defines a holder 4025 for positioning a gel matrix 12 (FIG. 20) between electrodes 20 and 22 for separating particles using a tracking dye. In this exemplary embodiment, an electrophoresis controller 4110 may include a sensor 4200 positionable adjacent to the gel matrix, a controller 4300 (FIG. 21) connectable to an electrical power source 30 (FIG. 20) and to a power supply 50 (FIG. 20) for providing a voltage across the electrodes of the electrophoresis apparatus, and a transmitter 4600 (FIG. 21) such as a wireless transmitter operably connectable to a communications network 15. The controller may be disposed in the housing with various controls (knobs, dials, indictors, and/or lights) disposed on the outside of the housing. Another embodiment of an electrophoresis apparatus may be realized by incorporating controller 300 (FIG. 1) into the high voltage power supply 50 (FIG. 1).

Sensor 4200 may be operably connected to controller 4300 (FIG. 21) via a cable 4254 (FIG. 20). As described above, controller 4300 (FIG. 21) may be essentially the same controller 300 (FIG. 1) and operable for turning off electrical power to power supply 50 based on a change in light from the illuminated gel matrix, such as light reflected from the illuminated gel, due to migration of the tracking dye into the illuminated gel matrix.

For example, electrophoresis apparatus 4110 may include an electrical plug 4330 (FIG. 20) electrically connectable to electrical power source 30 such as an outlet for receiving 120 volt alternating current (AC) for powering electrophoresis apparatus 4110. Electrophoresis apparatus 4110 may also have an electrical socket 4340 (FIG. 20) electrically connectable to an electrical plug 52 (FIG. 20) of power supply 50 (FIG. 20) for supplying 120 volt alternating current to power supply 50 (FIG. 20). Power supply 50 (FIG. 20) may be connected via wires 54 and 56 (FIG. 20) for supplying direct current such as about 1 volt to about 100 volts direct current (DC) to electrodes 20 and 22, respectively, of electrophoresis apparatus 4110. Controller 4300 (FIG. 21) is operable for turning off electrical power to power supply 50 (FIG. 20), and thus, turning off the supply of direct current to electrodes 20 and 22.

In one embodiment, sensor 4200 may be positionable under or alongside electrophoresis apparatus 4110. Sensor 4200 may be similar to sensor 200 (FIG. 1), sensor 260 (FIG. 4), and sensor 1200 (FIG. 16), and may include an ambient light sensor 2250 (FIG. 18). The controller and/or transmitter may operably send a phone or text message remotely via communications network indicating the cessation of an experiment.

Figure 22:
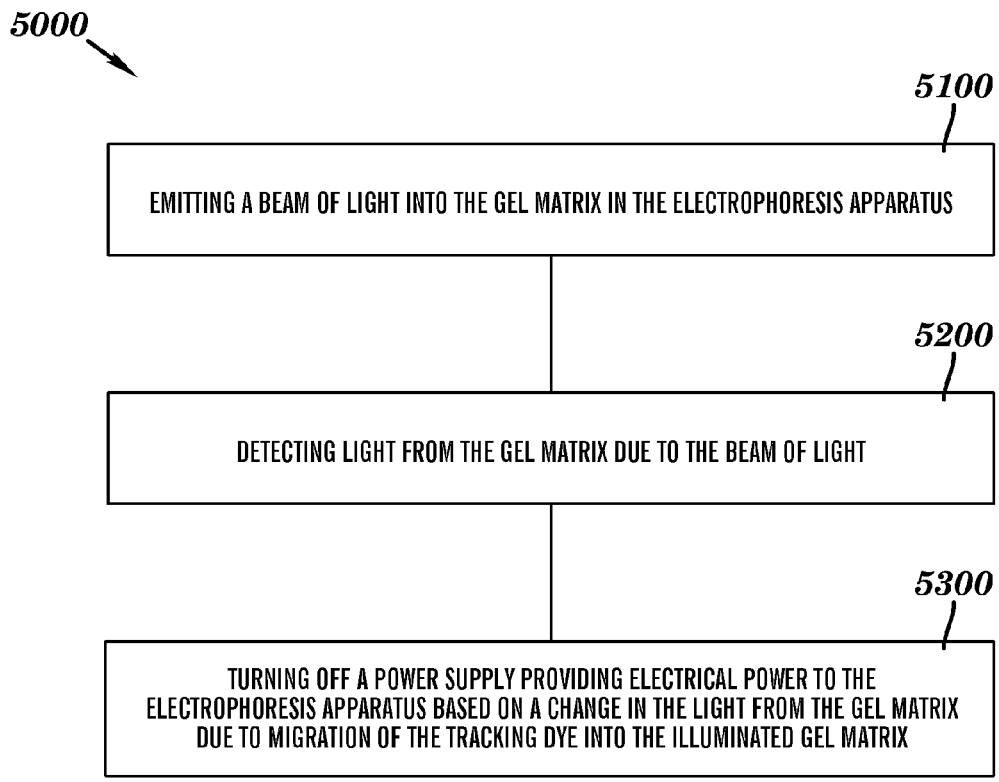
FIG. 22 is a flowchart of a method for controlling an electrophoresis process in accordance with aspects of the present disclosure.

FIG. 22 is a flowchart of a method 5000 for controlling an electrophoresis process in accordance with aspects of the present disclosure. The method includes at 5100, emitting a beam of light into the gel matrix in the electrophoresis apparatus, at 5200, detecting light from the gel matrix due to the beam of light, and at 5300, turning off a power supply providing electrical power to the electrophoresis apparatus based on a change in the light from the gel matrix due to migration of the tracking dye into the illuminated gel matrix.

Figure 23:
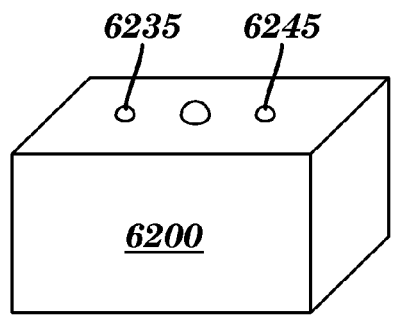
FIG. 23 is another embodiment of a sensor in accordance with aspects of the present disclosure.
Figure 24:
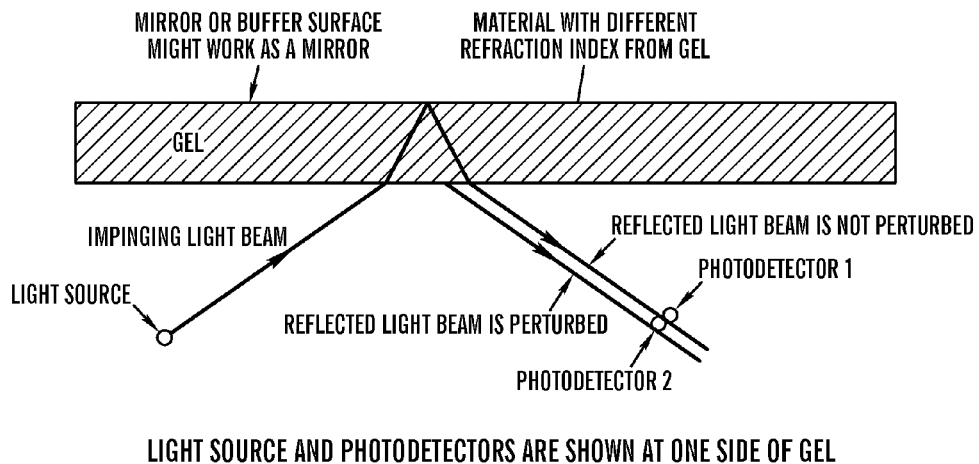
FIGS. 24 and 25 are schematic illustrations of the sensor shown in FIG. 23.
Figure 25:
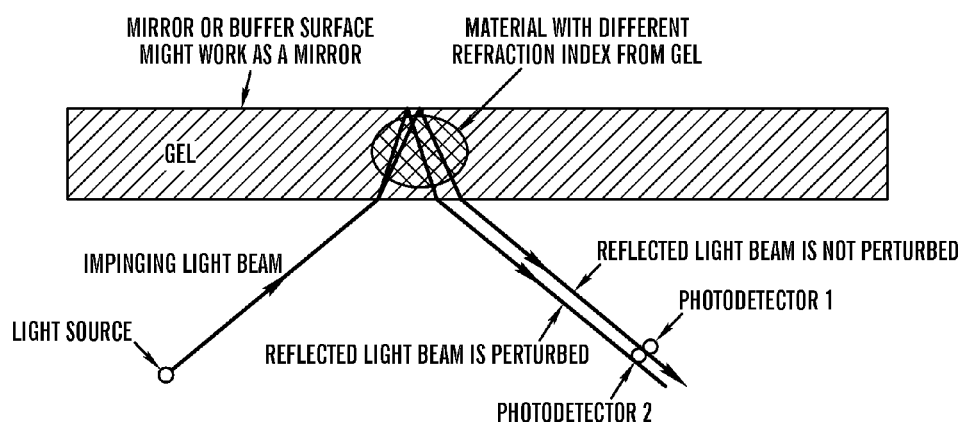

FIG. 23 is another embodiment of a sensor 6200 having a light detector comprising a refractive index detector 6235 and 6245. As shown in FIGS. 24 and 25, the light emitter and photodetector may work as a system to detect changing of the refraction index in the gel due to migrating molecules that change the path of emitted light. The light source is placed in the cavity of the housing located on the same side of two detectors. Cavities of these three elements: two photodetectors and a light source may have axes that have one point of crossing into the gel. The two photosensors of the controller may be balanced at the beginning of the electrophoresis process. Appearance of any migrated molecules in the path of the light source will throw off the balance and will cause alarm activation. The light source may be located under or above the gel.

In the above described embodiments, the light source may be a light emitting diode which emits light having a generally narrow band width of wavelengths. For example, the light emitting diode may be operable to emit light having generally a wavelength between about 550 nanometers and about 650 nanometers, and preferably between about 600 nanometers and about 625 nanometers.

As described above, in gel electrophoresis experiments, "loading dye" is used to aid determination of when the components of a mixture that are being separated or partitioned within a "gel" have traveled the maximum distance, marking the end of the experiment. From the present description, it will be appreciated that the technique of the present disclosure overcomes the problems due to the unpredictable time required to complete each experiment, and the need to constantly monitor the system by watching the slow migration of the dye. For example, the present technique may save researchers, technicians, clinicians, forensics scientists, students and others from (a) the wasteful and woefully inconvenient task of "babysitting" the electrophoresis run in order to shut it off before the experiment is ruined; and (b) inconsistencies in run-time from experiment to experiment. The present technique also avoids significant time lost in this exercise, both because of the constant monitoring, and also because if one is not available to stop the experiment as soon as the dye has traveled to the end of the gel, the experiment can be ruined with complete loss of results. As described above, the present technique provides a portable sensor/controller that detects the completion of electrophoresis gel experiments and triggers the power supply unit to turn itself off while at the same time releasing an audio signal to indicate the cessation of the experiment. The controller may also include a wireless transmitter for sending a phone or text message remotely via a communications network 15 (FIG. 1), indicating the cessation of the experiment. For example, the text messaging may employ a wireless GSM SIM card that sends a message to the end user indicating the end of the experiment. The use of a SIM card makes the sensor operable without the need of a phone line or internet jack. The sensor may be tailored to operate with a specific loading dye. In addition, the present technique may be implemented to improve the functionality of existing electrophoresis systems.

Figure 26:
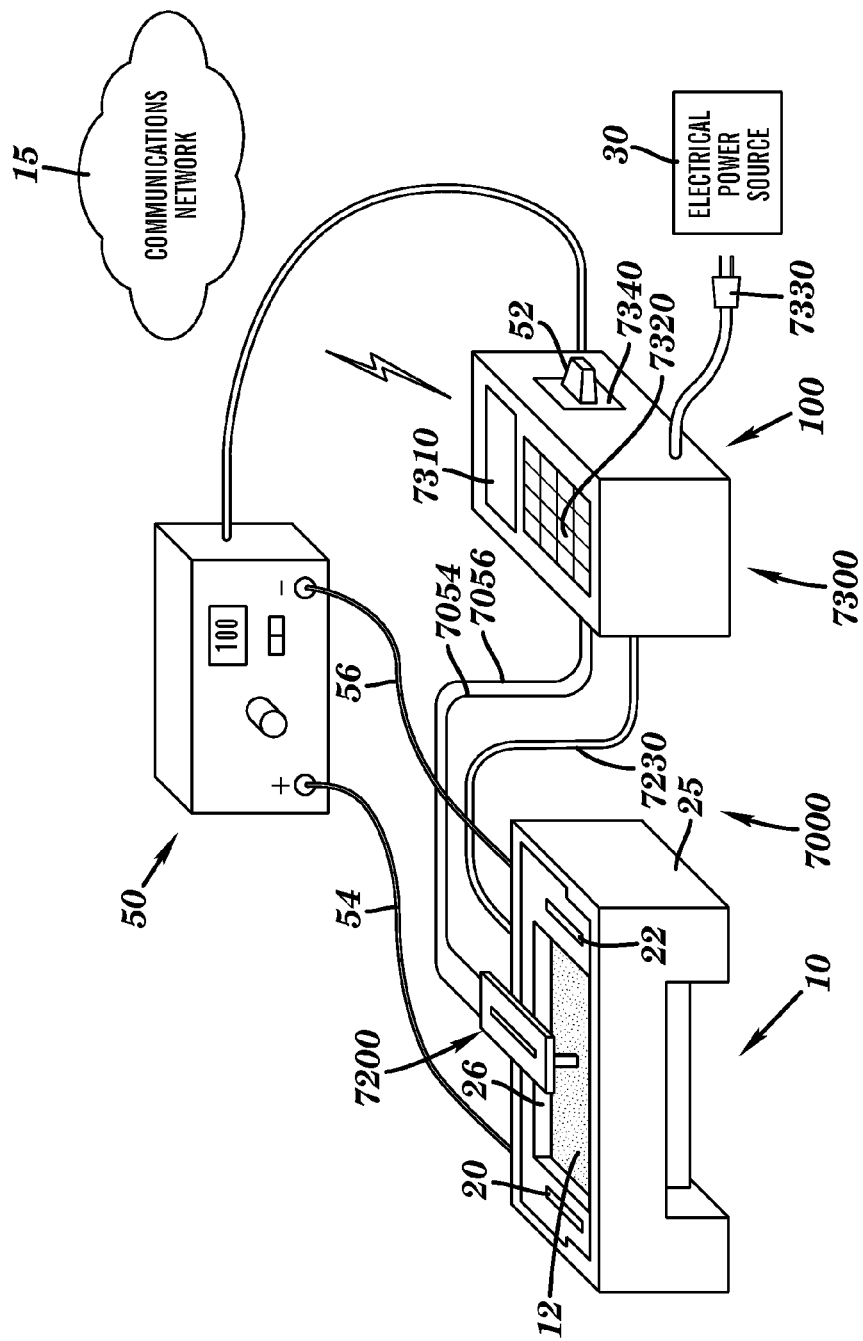
FIG. 26 is a perspective view of another embodiment of an electrophoresis controller in accordance with aspects of the present disclosure.
Figure 29:
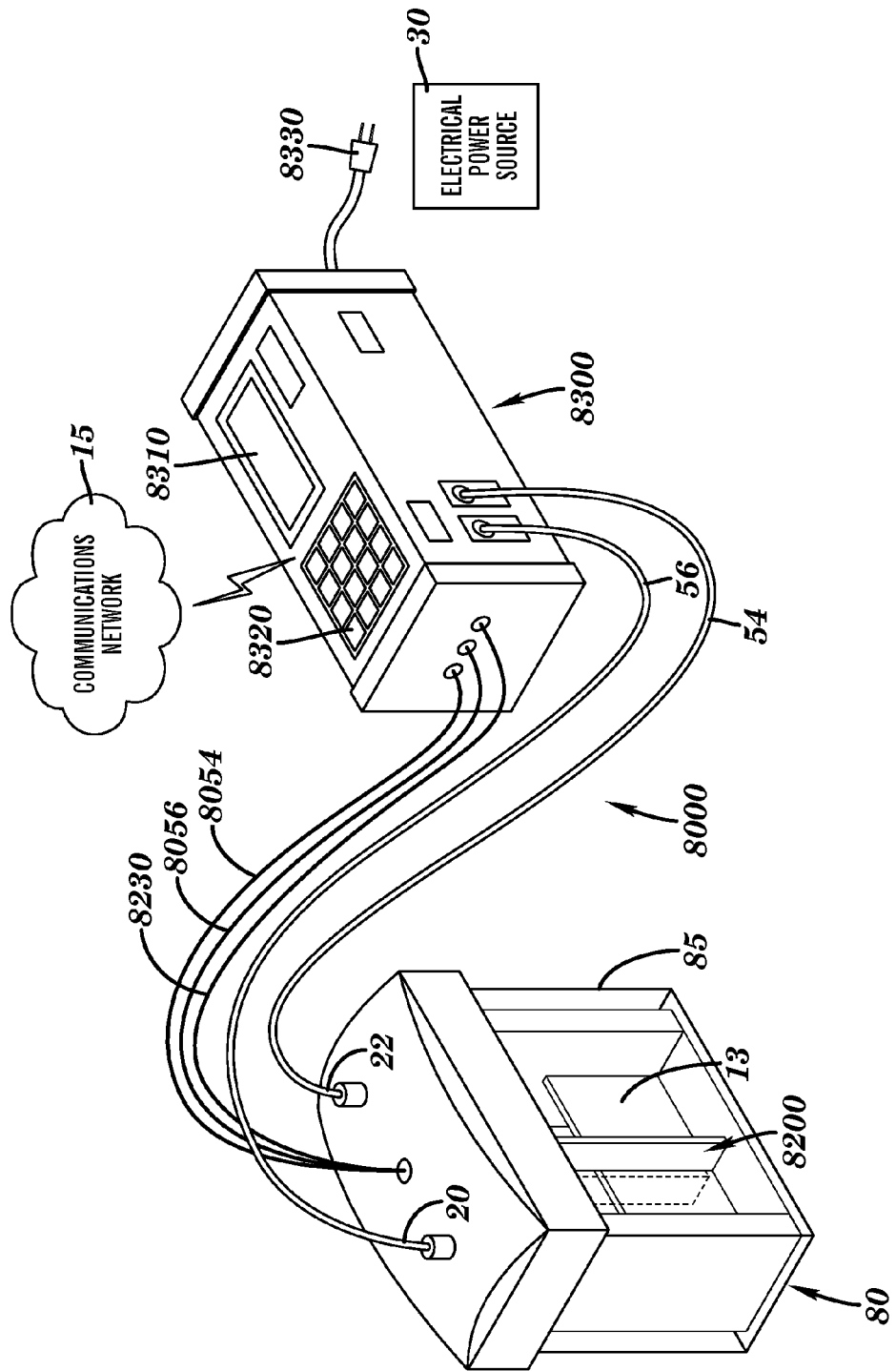
FIG. 29 is a perspective view of another embodiment of an electrophoresis controller in accordance with aspects of the present disclosure.

FIGS. 26 and 29 illustrate further embodiments of electrophoresis controllers in accordance with aspects of the present disclosure. For example, as shown in FIG. 26, an electrophoresis controller 7000 may be operable with agarose or horizontally-orientated gel systems, and as shown in FIG. 29, an electrophoresis controller 8000 may be operable with polyacrylamide or vertically-orientated gel electrophoresis systems. The electrophoresis controllers in accordance with aspects of the present disclosure may be employed to be readily adapted to fit a range of existing systems. In addition, such electrophoresis controller may be incorporated into and be a part of an electrophoresis system.

As described in greater detail below, such electrophoresis controllers may generally employ directing light onto the gel matrix and monitoring the light passing through the gel to detect the migrating dye, e.g., the mode of detection may be by direct line of sight interference by the migrating dye. In some embodiments, a sensor system may include a light emitter such as light guide or a fiber optic cable used for receiving light passing through the gel matrix and delivering such light to a remotely located light receiver such as a photodetector. The light guide or fiber optic cable may be a cable containing one or more optical fibers that are used to carry light. The optical fiber elements are typically individually coated with plastic layers and contained in a protective tube. In some embodiments, two light emitting diodes (LEDs) may be employed, e.g., one LED being employed as a light emitter such as a transmitting LED and the other LED being employed as a light receiver such as a photodetector. As explained in greater detail below, the light source, such as an LED, for transmitting light may transmit a narrow wavelength band of light, and the photodetector, such as an LED, for receiving the light may selectably detect a narrow wavelength band of light. In some embodiments, the transmitted narrow wavelength band of light may be different from the selectably detectable narrow wavelength band of light.

With reference again to FIG. 26, electrophoresis controller 7000 may be operably connectable to an electrophoresis apparatus 10 having a holder 25 for positioning a gel matrix 12 horizontally between electrodes 20 and 22 for separating particles using a tracking dye. In this exemplary embodiment, electrophoresis controller 7000 may include a sensor system 7200 positionable adjacent to the gel matrix, a controller 7300 connectable to an electrical power source 30 and to a power supply 50 for providing a voltage across the electrodes of the electrophoresis apparatus. Controller 7300 may include an output device 7310 such as a display, an input device 7320 such as a keyboard, and a transmitter (not shown in FIG. 26) such as a wireless transmitter operably connectable to a communications network 15. Other input and output devices may be employed, e.g., a touchscreen. Sensor system 7200 may be operably connected to controller 7300 via a plurality of cables. For example, sensor system 7200 may be operably connected to controller 7300 via a light guide 7230 such as a fiber optic cable, and electrical wires 7054 and 7056. As described in greater detail below, controller 7300 is operable for monitoring a change in light from the illuminated gel matrix, such as light passing through the gel matrix due to migration of the tracking dye into the illuminated gel matrix. Controller 7300 may also be operable to turn off electrical power to power supply 50 based on a change in light from the illuminated gel matrix, such as light passing through the gel matrix due to migration of the tracking dye into the illuminated gel matrix.

For example, controller 7300 may include an electrical plug 7330 electrically connectable to electrical power source 30 such as an outlet for receiving 120 volt alternating current (AC) for powering electrophoresis controller 7000. Controller 7300 may also have an electrical socket 7340 electrically connectable to an electrical plug 52 of power supply 50 for providing 120 volt alternating current to power supply 50. Power supply 50 may be connected via electrical wires 54 and 56 for providing direct current (DC) such as 1 volt to 200 volts direct current to electrodes 20 and 22, respectively, of electrophoresis apparatus 10. In one embodiment, controller 7300 is operable for turning off electrical power to power supply 50, and thus, turning off the supply of direct current to electrodes 20 and 22. In other embodiments, the power supply may be directly operably connected to electrical power source 30.

Figure 27:
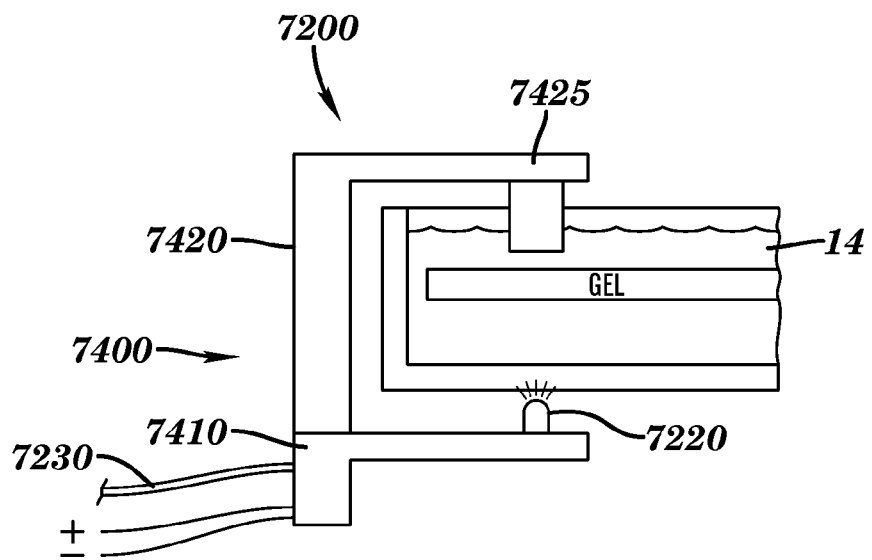
FIG. 27 is an enlarged side elevational view of the sensor system and a portion of the electrophoresis apparatus of FIG. 26.
Figure 28:
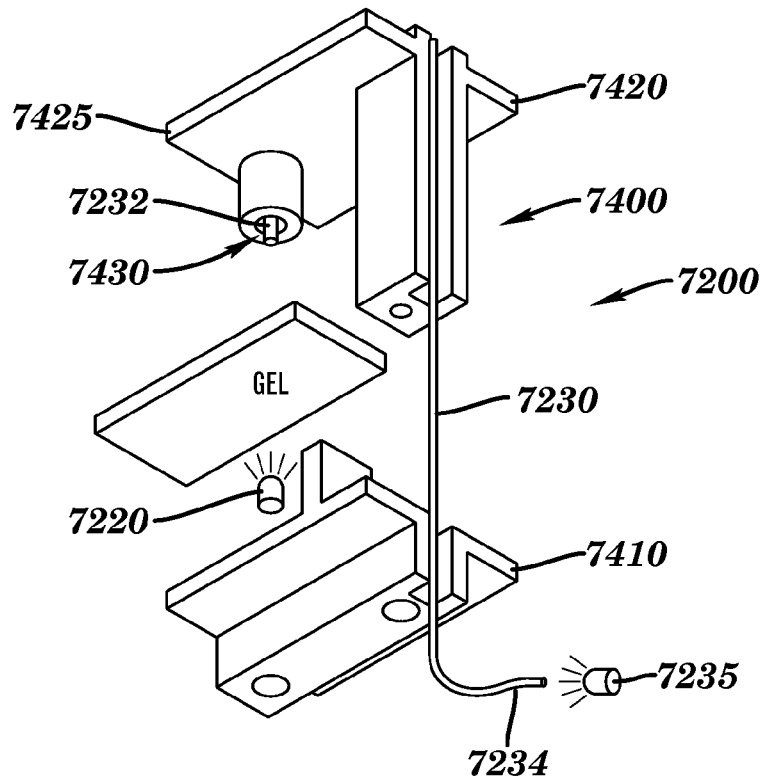
FIG. 28 is an enlarged exploded perspective view of the sensor system and a portion of the gel matrix of FIG. 26.

In one embodiment, sensor system 7200 is positionable adjacent to a gel matrix. For example, sensor system 7200 may be positionable over a side edge or wall such as the front or rear side edge or wall of electrophoresis apparatus 10. For example, sensor 7200 may be horizontally positionable along the front or rear side edge or wall of electrophoresis apparatus 10. In other embodiments, a sensor system may be configured, movable and positionable horizontally along the side edges or walls of an electrophoresis apparatus. As shown in FIGS. 27 and 28, sensor system 7200 may include a support 7400, a light emitter 7220 such as a light source, and a light receiver 7230 such as a light guide or a fiber optic cable. Support 7400 may include a first portion 7410 positionable on one side of the gel matrix, and a second portion 7420 positionable on the other opposite side of the gel matrix. Light source 7220 may be disposed on the first portion of the support for directing light onto the gel matrix. Light guide 7230, such as a fiber optic cable, may be positionable on the second portion of the support with a first end 7232 (FIG. 28) of light guide 7230 facing the gel matrix for receiving light emitted from light source 7220 which passes through the gel matrix. The light source and the first end of the light guide may be vertically aligned with each other. A light detector 7235 (FIG. 28) may be disposed remote from the sensor system in controller 7300 (FIG. 26) for receiving light from a second end 7234 of the light guide for detecting light from the illuminated gel matrix.

Other features of support 7200 may include second portion 7420 defining a shield 7425 for shielding ambient light from the first end of the light guide. Second portion 7420 may also define a passageway 7430 (FIG. 28) through which the first end of the light guide is positionable such as positionable prior to an opening of the passageway. Such a configuration may also shield the end of the light guide from ambient light. Support 7200 may have a generally C-shaped configuration or U-shaped configuration. As shown in FIG. 27, the first end of the light guide and/or a portion of the second support may be disposable in a buffer 14 in the electrophoresis apparatus. From the present description, it will be appreciated that the downward facing or positioning of the receiver optics at the top of the support may reduce the possibility of interference from shadows and ambient light, the fiber optic cable may be sensitive to only a narrow beam of light positioned, directed, or focused directly into its end or aperture, the fiber optic cable may be resistant to electrical noise and other interferences that would inhibit transmission or effect transmission through a conventional signal wire such as an electrical wire, the photodetector may be encased and sensitive to a narrow wavelength of light, the photodetector may be positioned any distance way from the support because light transmission through the fiber optic cable is generally not affected by the typical length of the cable for this application, and the support may be attached to the side of the electrophoresis chamber and moveable up or down and positioned at a point where the end user wants the experiment to end.

From the present description, it will be appreciated that a sensor system in accordance with aspects of the present disclosure may include switching the positioning of the light receiver such as the guide and the light emitter such as the light source as shown in FIGS. 27 and 28. For example, an end of a light guide such as a fiber optic cable may be positioned facing upwardly on the first portion of the support, and a light source, such as an LED light source, may be positioned on the second portions of the support facing downwardly. The end of the light guide may face upward and be disposed within a passageway such as positionable prior to an opening in a passageway to limit light reaching the end of the light guide and reducing the effect of changes in ambient light. The light source may be suitably waterproofed so that the light source may be place in the buffer solution.

With reference again to FIG. 29, electrophoresis controller 8000 in accordance with aspects of the present disclosure may be operably connectable to an electrophoresis apparatus 80 having a holder 85 for positioning a gel matrix 13 vertically between electrodes 20 and 22 for separating particles using a tracking dye. In this exemplary embodiment, electrophoresis controller 8000 may include a sensor system 8200 positionable adjacent to the gel matrix, and a controller 8300 connectable to an electrical power source 30. For example, sensor system 8200 may be horizontally and vertically, movable and positionable along the front or rear side edge or wall of electrophoresis apparatus 80. In this embodiment, controller 8300 may include a power supply for providing a voltage across the electrodes of the electrophoresis apparatus. Controller 8300 may include an output device 8310 such as a display, an input device 8320 such as a keyboard, and a transmitter (not shown in FIG. 29) such as a wireless transmitter operably connectable to a communications network 15. Other input and output devices may be employed, e.g., a touchscreen. Sensor system 8200 may be operably connected to controller 8300 via a plurality of cables. For example, sensor system 8200 may be operably connected to controller 8300 via a light guide 8230 such as a fiber optic cable, and electrical wires 8054 and 8056. As described in greater detail below, controller 8300 is operable for monitoring a change in light from the illuminated gel matrix, such as light passing through the gel matrix due to migration of the tracking dye into the illuminated gel matrix. Controller 8300 may also be operable to turn off electrical power to the electrophoresis apparatus based on a change in light from the illuminated gel matrix, such as light passing through the gel matrix due to migration of the tracking dye into the illuminated gel matrix.

For example, controller 8300 may include an electrical plug 8330 electrically connectable to electrical power source 30 such as an outlet for receiving 120 volt alternating current (AC) for powering electrophoresis controller 8000. Controller 8300 may be connected via electrical wires 8054 and 8056 for providing direct current (DC) such as 1 volt to 100 volts direct current to electrodes 20 and 22, respectively, of electrophoresis apparatus 80. In one embodiment, controller 8300 is operable for turning off electrical power to electrophoresis apparatus 80, and thus, turning off the supply of direct current to electrodes 20 and 22.

Figure 30:
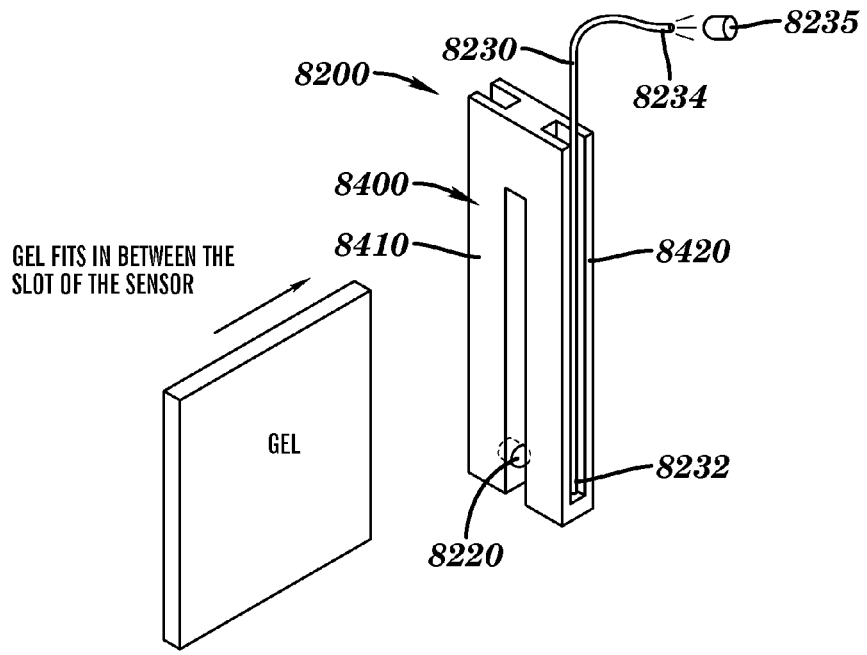
FIG. 30 is an enlarged perspective view of the sensor system and a portion of the gel matrix of FIG. 29.

In one embodiment, sensor system 8200 is positionable adjacent to a gel matrix. For example, sensor system 8200 may be slidably positionable over a vertically extending gel matrix. As shown in FIG. 30, sensor system 8200 may include a support 8400, a light emitter 8220 such as a light source, and a light receiver 8230 such as light guide such as a fiber optic cable. Support 8400 may include a first portion 8410 positionable on one side of the gel matrix, and a second portion 8420 positionable on the other side of the gel matrix. Light source 8220 may be disposed on the first portion of the support for directing light onto the gel matrix. Light guide 8230, such as a fiber optic cable, may be positionable on the second portion of the support with a first end 8232 of light guide 8230 facing the gel matrix for receiving light emitted from light source 8220 which passes through the gel matrix. The light source and the first end of the light guide may be horizontally aligned with each other. A light detector 8235 may be disposed remote from the sensor system in controller 8300 (FIG. 29) for receiving light from a second end 8234 of the light guide for detecting light from the illuminated gel matrix.

Figure 31:
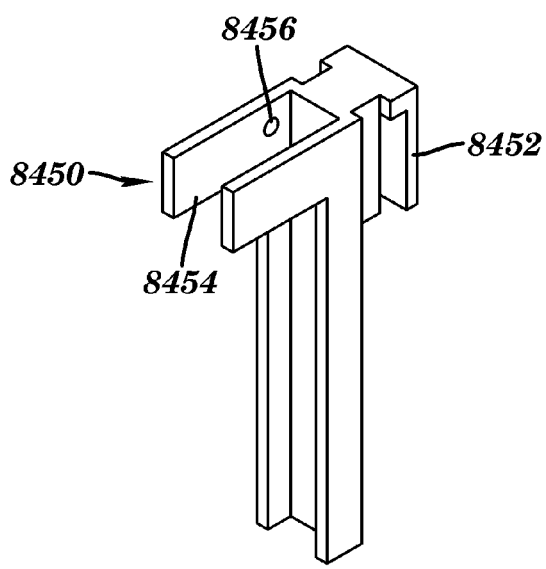
FIG. 31 is an enlarged perspective view of a clip for supporting the sensor system in the electrophoresis controller of FIG. 29.

As shown in FIG. 31, a mounting clip 8450 may be operably attachable to support 8400 for vertically and horizontally positioning the light source and the first end of the light guide along a vertically-extending gel matrix. For example, the mounting clip may provide up and down as well as side-to-side movement of the support. Mounting clip 8450 may include a first portion 8452 supportable on the electrophoresis apparatus and a second portion 8454 defining a channel 8455 for receiving first or second portion 8410 (FIG. 30) or 8420 (FIG. 30) of support 8400 (FIG. 30) and releasably attaching to support 8400 (FIG. 30) such as with a screw extendable through an aperture 8456. As shown in FIG. 29, a portion of sensor system 8200 is submerged in the buffer and operable to receive a reliable signal from the migrating dye. The light guide and the light source may be operably waterproofed.

Figure 32:
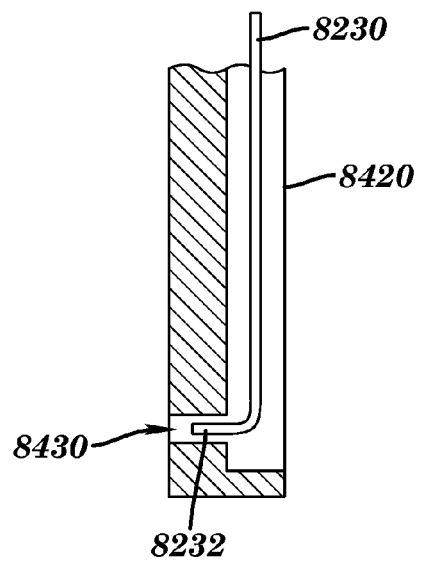
FIG. 32 is a cross-sectional view of the lower end portion of the sensor system having the light guide of FIG. 30.

With reference to FIG. 32, other features of the support may include second portion 8420 defining a shield for shielding ambient light from the first end of the light guide. Second portion 8420 may also define a passageway 8430 through which the first end 8232 of the light guide 8230 is positionable such as positionable prior to an opening of the passageway. Support 8200 may have a generally C-shaped configuration or U-shaped configuration. Lower portions of support 8200 may be disposable in a buffer of the electrophoresis apparatus. From the present description, it will be appreciated that the positioning of the receiver optics may reduce the possibility of shadows and ambient light interference, the fiber optic cable may be sensitive to only a narrow beam of light positioned directly at its aperture, and the receiving photodetector may be sensitive to a narrow wavelength of light, and it can be positioned any distance way from the support.

Figure 33:
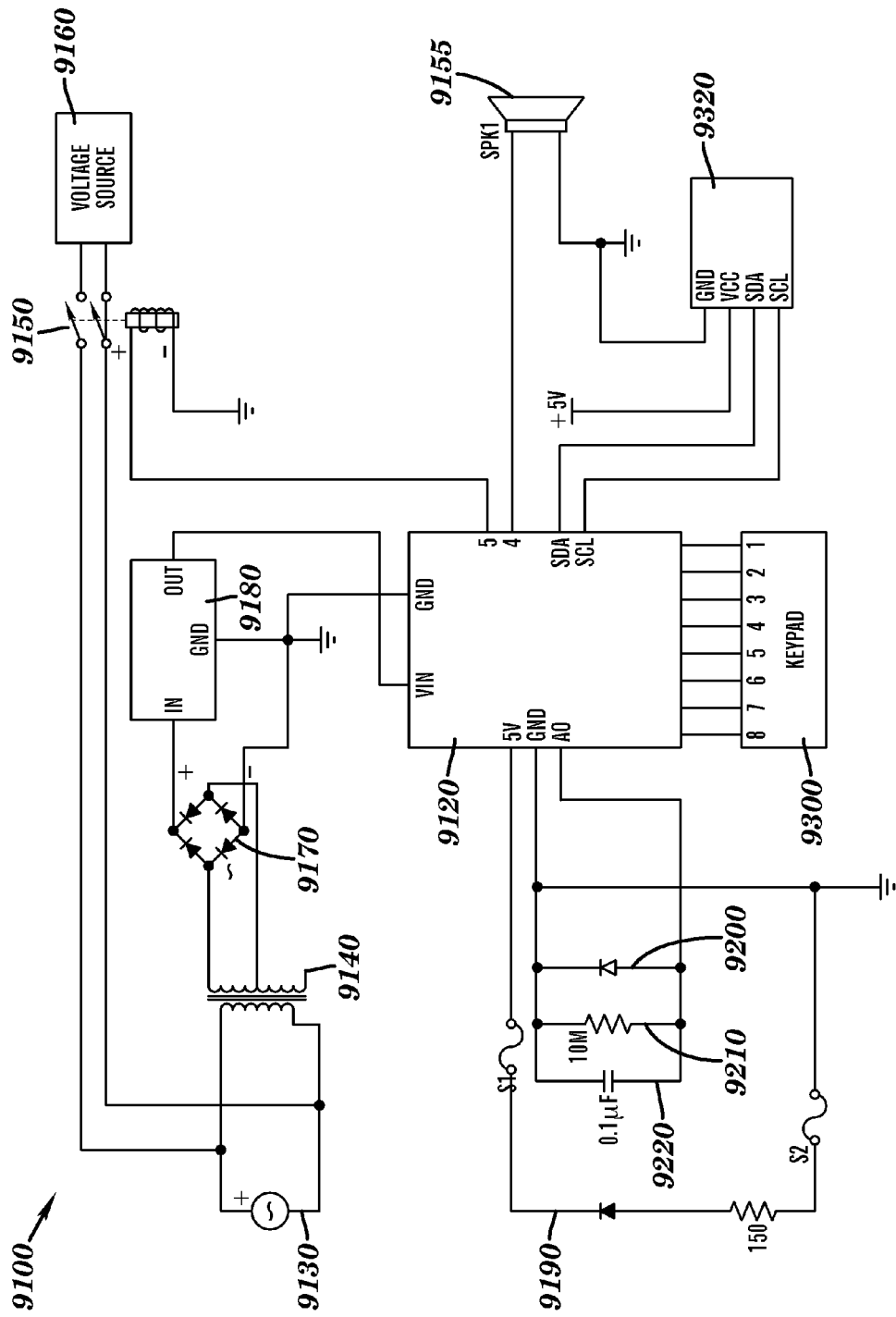
FIG. 33 is a schematic illustration of one embodiment of a controller in accordance with aspects of the present disclosure for use in the electrophoresis controllers of FIGS. 26 and 29.

FIG. 33 illustrates an embodiment of an electrophoresis controller 9100 in accordance with aspects of the present disclosure for use in, for example, the electrophoresis controllers of FIGS. 26 and 29. In this illustrated embodiment, a microcontroller 9120 may be powered from the wall. For example, electricity may enter the system through a power module 9130. From there electrical power may operably go to a transformer 9140, and to a relay 9150, where it powers a voltage source 9160. The transformer steps down the voltage into 12 volts alternating current (AC) with a current of 1.6 amperes (A). The current is passed through a voltage rectifier 9170, which converts the signal from AC to DC. To protect the circuit, the power may be passed through a voltage regulator 9180 before being fed into microcontroller 9120. The microcontroller may be a single-board microcontroller.

A voltage is applied to the light source 9190 such as an LED which shines light towards receiving LED 9200 which in turn converts the light energy to a voltage signal. Receiving LED 9200 may be wired in parallel with a 10 MΩ resistor 9210. An anode of the receiving LED may be fed into the microcontroller where it reads the voltage value. A 0.1 µF capacitor 9220 is added in parallel cancels out electrical noise. A keypad 9300 allows for user input. Users can choose what type of dye they wish to use, whether or not the control unit will cut off the power supply to the voltage source, and have the ability to enter in a telephone number so that the control unit will then send a text message to the indicated number. The user may receive feedback from the system via a display 9320 such as an LCD2004 LCD monitor. A PCF8574T I/O expander chip may be employed to allow for inter-integrated circuit (I2C) communication between the microcontroller and the display. A GSM shield may be mounted on top of the microcontroller to allow for SMS communications. This allows a user to enter a ten digit phone number to which the control unit will send a text message. A SIM card may be required for this function. The microcontroller may also control two outputs: a relay 9150 and a piezzo buzzer 9155. When a true signal is recognized, the piezzo buzzer may be activated for an appropriate time interval to convey the condition to a user. In addition, upon user request, a DPST NC relay with a coil voltage of 5V may be activated, which cuts off the power supply to the voltage source.

Figure 34:
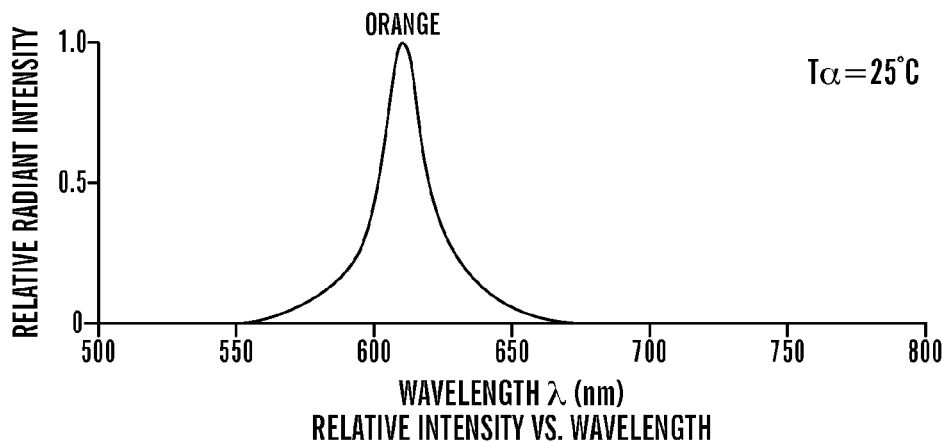
FIGS. 34 and 35 are emission spectra of orange and red light emitting diodes, respectively.
Figure 35:
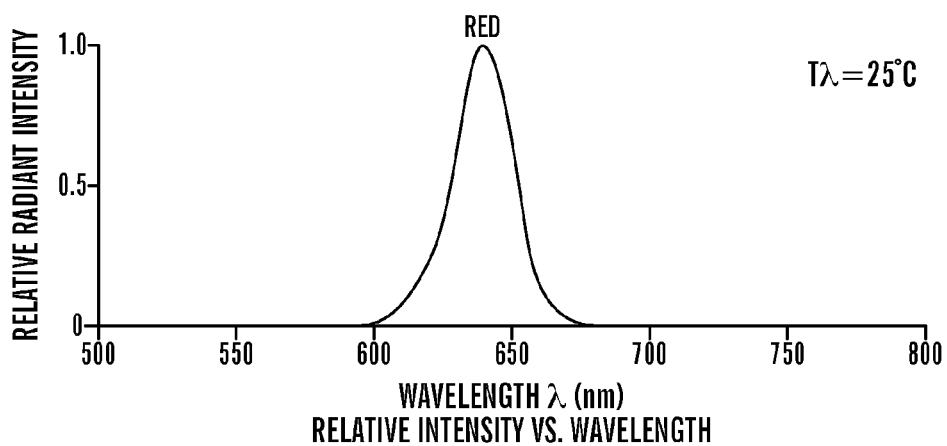

In the various embodiments, the electrophoresis controllers may employ light emitting diodes (LEDs) for both emitting light and detecting light. For example, two LEDs, one orange transmitting LED and one red receiving LED may be operably employed to send and received light signals through the gel. As will be appreciated, from the present discussion, this pair of LEDs was selected because the orange LED transmits a narrow beam of light. For example, FIGS. 34 and 35 illustrate emission spectra of orange and red light emitting diodes, respectively. In addition, contrary to the common usage of LED as a light source, LEDs are operable to receive a narrower bandwidth of light (compared to photodiodes) a few nanometers below their radiant peak intensity. Therefore, the red LED was selected to receive a narrow wavelength of light that has the peak absorption range for bromophenol blue (BB) and xylene cyanol (XC) which may be employed as color markers to monitor the process of agarose gel electrophoresis and polyacrylamide gel electrophoresis.

Figure 36:
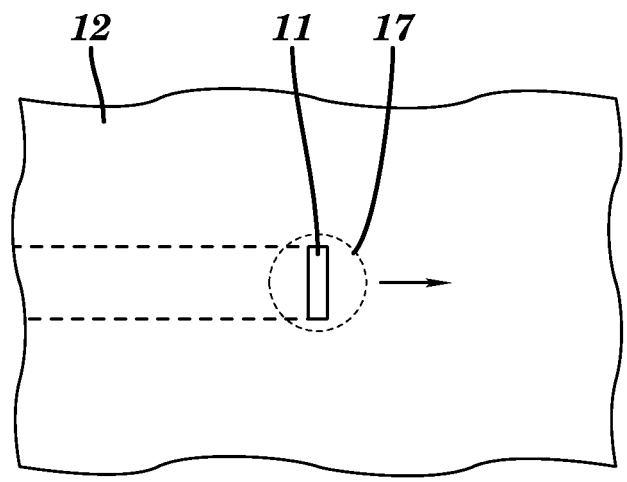
FIGS. 36 and 37 are views of a portion of the gel matrix and migrating dye in which a portion of the gel matrix is illuminated by a light source.
Figure 37:
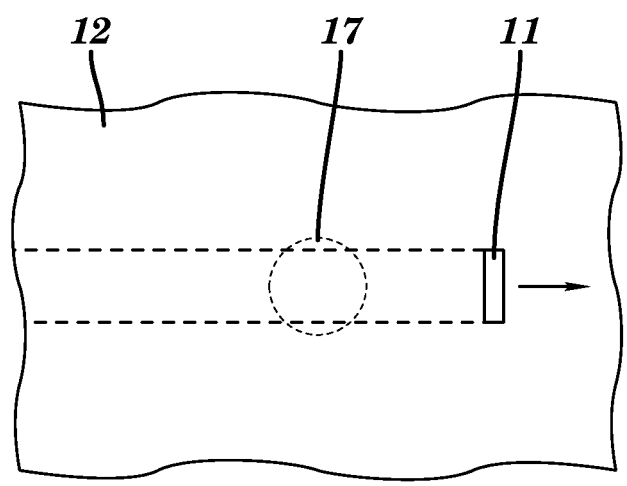

The mode of detection may be by direct line of sight interference by the migrating dye. The transmitting LED shines light through the gel and it is received by a light guide such as a fiber optic cable that transmits a received light to a receiving photodiode or LED which in turn generates a voltage signal of about 1.5 V. As shown in FIG. 36, when the migrating dye 11 passes through the line of sight of the transmitted light 17, the dye absorbs a portion of the light and reduces the voltage signal to below 0.6 volts. The voltage goes back up to 1.5 volts when the migrating dye 11 migrates out of the line of sight of the transmitted light 17, as shown in FIG. 37.

Figure 38:
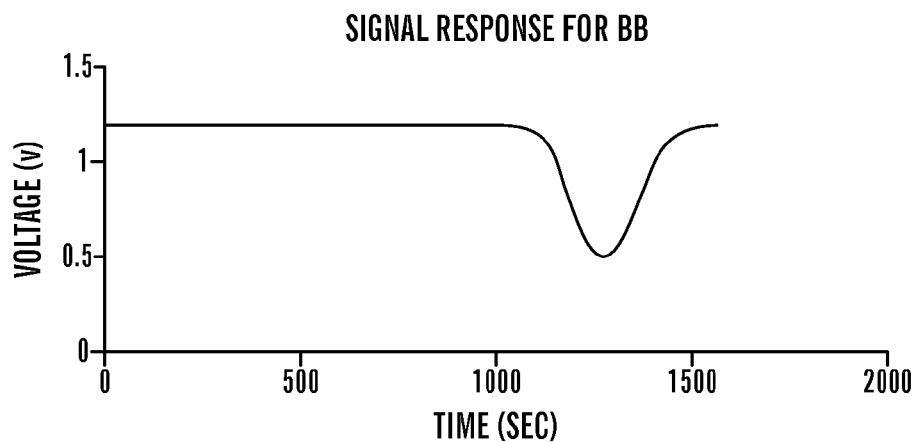
FIG. 38 is a graphical illustration of signal response for bromophenol blue (BB)
Figure 39:
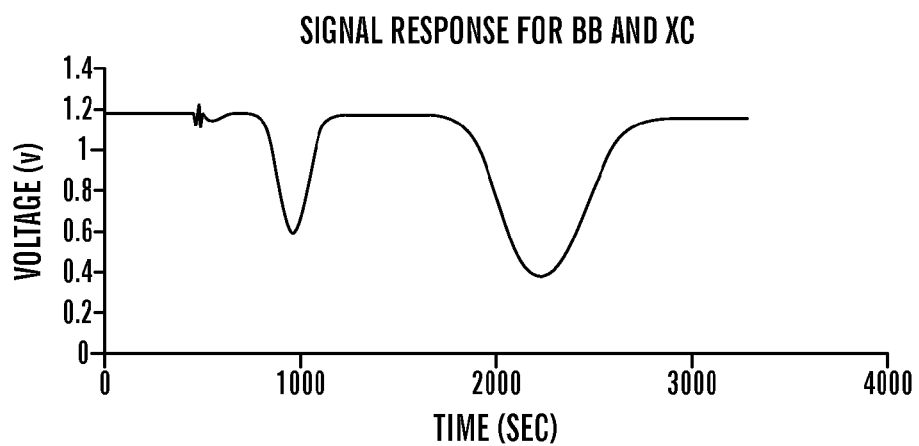
FIG. 39 is a signal response for bromophenol blue (BB) and xylene cytanol (XC)

When one dye is used for an experiment, the detector or controller monitors and looks for a high to low to high voltage signal change for example as shown in FIG. 38. Such change may be employed to trigger various operations such as sending a message or signaling the user, turning off the power to the terminals or turning off the power supply, or reducing or alternating the polarity of power across the gel. When a mixture of two dyes of different migration rates are used, the detector or controller may monitor or look for a high to low to high voltage signal change for the passing of the first dye, then a low to high signal voltage change for the passing of the second dye as shown in FIG. 39. Such change maybe employed to trigger various operations such as sending a message or signaling the user, turning off the power to the terminals or turning off the power supply, or reducing or alternating the polarity of power across the gel.

Figure 40:
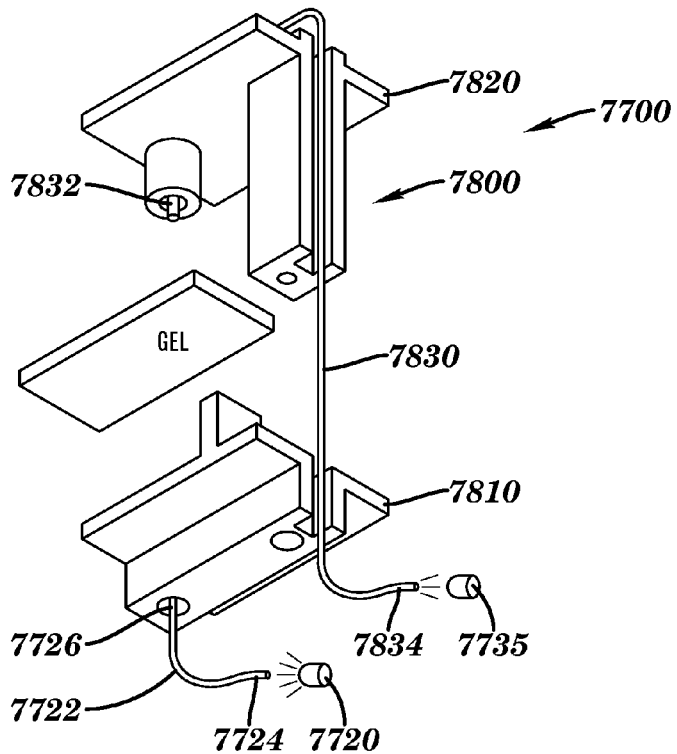
FIG. 40 is an exploded perspective view of another embodiment of a sensor system and a portion of the gel matrix in accordance with aspects of the present disclosure.

With reference to FIG. 40, in another embodiment a sensor system 7700 may include a support 7800, a light source 7720, a light emitter 7722 such as a first light guide or a fiber optic cable, a light receiver 7830 such as a second light guide or a fiber optic cable, and a light detector 7735. For example, sensor system 7700 may be movable and positionable over a side edge or wall such as the front or rear side edge or wall of an electrophoresis apparatus. Support 7800 may include a first portion 7810 positionable on one side of the gel matrix, and a second portion 7820 positionable on the other side of the gel matrix. Light source 7720 may be directed toward a first end 7724 of light guide 7722, and a second end 7726 may be disposed on the first portion of the support for directing light such as directing light upwardly onto the gel matrix. Light guide 7830, such as a fiber optic cable, may be positionable on the second portion of the support with a first end 7832 of light guide 7830 facing the gel matrix for receiving light emitted from light source 7720 which passes through the gel matrix. End 7726 of light guide 7722 and end 7832 of light guide 7830 may be vertically aligned with each other. Light source 7720 and light detector 7735 may be disposed in a controller for emitting light into end 7724 of light guide 7722 and for receiving light from end 7834 of light guide 7830 for detecting light from the illuminated gel matrix.

Figure 41:
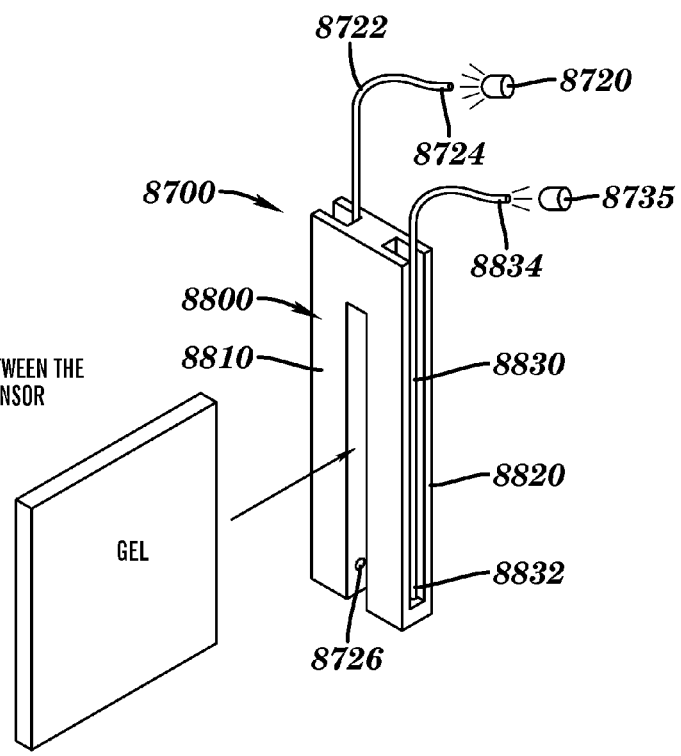
FIG. 41 is a perspective view of another embodiment of a sensor system and a portion of the gel matrix in accordance with aspects of the present disclosure.

With reference to FIG. 41, in another embodiment a sensor system 8700 may include a support 8800, a light source 8720, a light emitter 8722 such as a first light guide or a fiber optic cable, a light receiver 8830 such as a second light guide or a fiber optic cable, and a light detector 8735. For example, sensor system 8700 may be slidably positionable over a vertically extending gel matrix. Support 8800 may include a first portion 8810 positionable on one side of the gel matrix, and a second portion 8820 positionable on the other side of the gel matrix. Light source 8720 may be disposed adjacent to a first end 8724 of light guide 8722 for directing light to a second end 8726 onto the gel matrix. Light guide 8830, such as a fiber optic cable, may be positionable on the second portion of the support with a first end 8832 of light guide 8830 facing the gel matrix for receiving light emitted from end 8726 of light guide 8722 which passes through the gel matrix. End 8726 of light guide 8722 and end 8832 of light guide 8830 may be horizontally aligned with each other. Light source 8720 and light detector 8735 may be disposed remote from the sensor system in a controller for emitting light into end 8724 of light guide 8722 and for receiving light from end 8834 of light guide 7830 for detecting light from the illuminated gel matrix.

Figure 42:
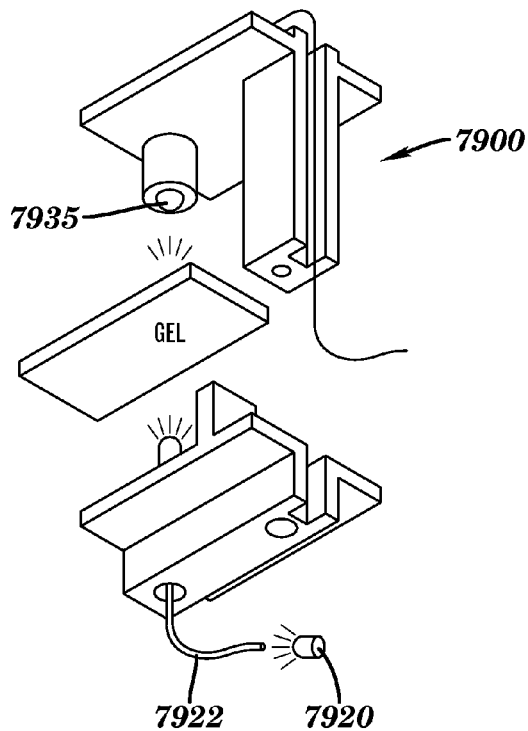
FIG. 42 is an exploded perspective view of another embodiment of a sensor system and a portion of the gel matrix in accordance with aspects of the present disclosure.

From the present description, in other embodiments, it will be appreciated that a sensor system in accordance with aspects of the present disclosure may include a light emitter that is operable to emit light onto the gel matrix. For example, as shown in FIG. 42, a sensor system 7900 may include a light emitter 7922 such as a light guide having an end for receiving light from a light source 7920, such as remote from the sensor system in a controller, and an end disposed on the sensor system for directing the light onto the bottom of the gel matrix. A light receiver 7935 such as a photodetector, which may be an LED employed as a photodetector, may be disposed on the support facing downwardly towards the gel matrix for receiving light emitted from light source 7922 which passes through the gel matrix. The photodetector may be disposed within a passageway, such as positionable prior to an opening of the passageway, to limit the light reaching the end of the photodiode and reducing the effect of changes in ambient light. The photodetector may be suitably waterproofed so that the photodetector may be place in the buffer solution.

From the present description, it will be appreciated that in other embodiments a sensor system in accordance with aspects of the present disclosure may include switching the positioning of the light emitter or light guide and the light receiver or photodetector shown in FIG. 42. For example, an end of a light guide such as a fiber optic cable may be positioned on a support facing downwardly for directing the light onto a top a gel matrix, and a photodetector, such as an LED employed as a photodetector, may be positioned facing upwardly towards the bottom of the gel matrix. The photodetector may be disposed within a passageway, such as positionable prior to an opening of the passageway, to limit the light reaching the end of the photodiode and reducing the effect of changes in ambient light.

Figure 43:
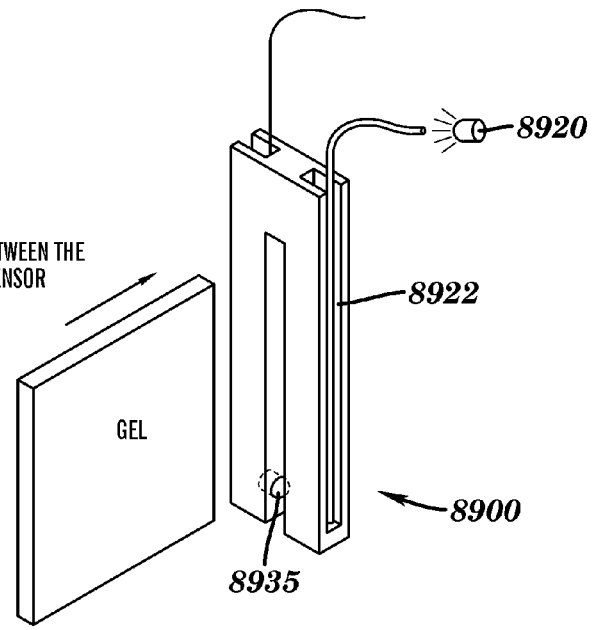
FIG. 43 is a perspective view of another embodiment of a sensor system and a portion of the gel matrix in accordance with aspects of the present disclosure.

With reference to FIG. 43, in other embodiments in accordance with aspects of the present disclosure, a sensor system 8900 may include a light emitter 8922 such as a light guide having an end for receiving light from a light source 8920 such as disposed remotely from the sensor system in a controller, and an end disposed on one side of the support for directing the light onto a side of a gel matrix. A light receiver 8935 such as a photodetector, which may be an LED employed as a photodiode, may be disposed on the other side of the support facing towards the gel matrix for receiving light emitted from light source 8922 which passes through the gel matrix. The photodetector may be suitably waterproofed so that the photodetector may be place in the buffer solution.

Figure 44:
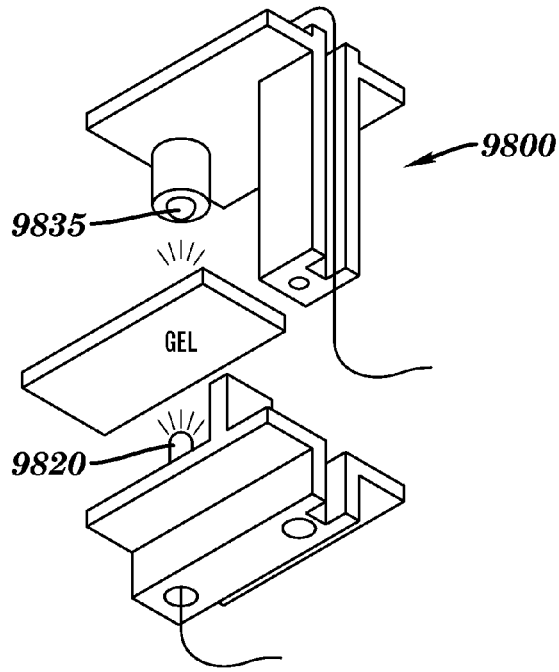
FIG. 44 is an exploded perspective view of another embodiment of a sensor system and a portion of the gel matrix in accordance with aspects of the present disclosure.

In other embodiments, it will be appreciated that a sensor system in accordance with aspects of the present disclosure may include a sensor system having a light emitter such as a light source and a light receiver such as a photodetector. For example, as shown in FIG. 44, a sensor system 9800 may include a light source 9820 disposed on a first portion of a support for directing light onto the gel matrix, and a photodetector 9835 disposed on a second portion of the support for detecting light from an opposite side of the illuminated gel matrix.

Figure 45:
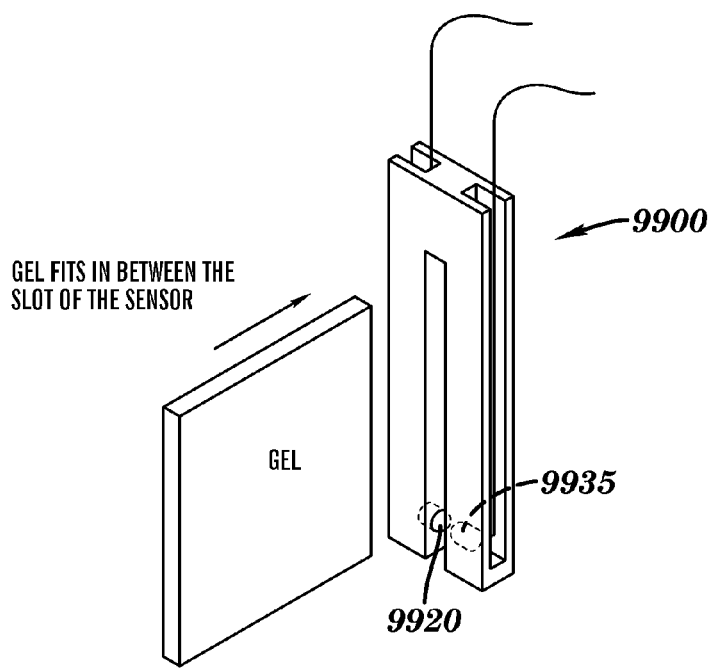
FIG. 45 is a perspective view of another embodiment of a sensor system and a portion of the gel matrix in accordance with aspects of the present disclosure.

In another example in accordance with aspects of the present disclosure, as shown in FIG. 45, a sensor system 9900 may include a light source 9920 disposed on a first portion of a support for directing light onto the gel matrix, and a photodetector 9935 disposed on a second portion of the support for detecting light from an opposite side of the illuminated gel matrix. The sensor may have a generally C-shaped or U-shaped configuration with a first portion positionable on one side of the gel matrix and a second portion positionable on a second side of the gel matrix. The light source and/or the photodetector may be waterproofed and disposable in the buffer solution. The photodetector may be an LED employed as a photodetector. In some embodiments, two light emitting diodes (LEDs) may be employed, e.g., one LED being employed as a transmitting LED and the other LED being employed as a photodetector. The light source, such as an LED, for transmitting light may transmit a narrow wavelength band of light, and the photodetector, such as an LED, for receiving the light may selectably detect a narrow wavelength band of light. In some embodiments, the transmitted narrow wavelength band of light may be different from the selectably detectable narrow wavelength band of light. For example, a red LED and/or an orange LED may be employed as a light source and/or a light detector.

From the present disclosure, it will be appreciated that the sensor systems described above for use with a horizontally disposed gel matrix may be used with a vertically disposed gel matrix. The sensor systems described above for use with a vertically disposed gel matrix may be used with a horizontally disposed gel matrix.

In addition, while a single light guide such as a single fiber optic cable may be employed in the sensor systems for transmitting light or receiving light, it will be appreciated that a plurality of light guides or a plurality of fiber optic cables may be employed for transmitting light or receiving light in the sensor systems.

Figure 46:
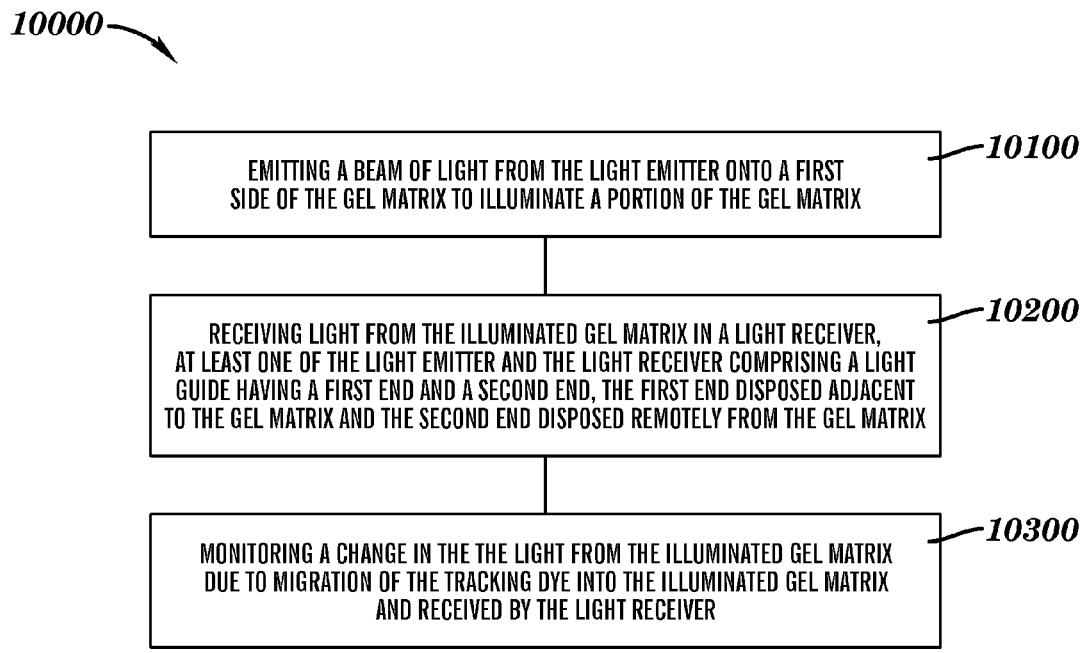
FIG. 46 is a flowchart of a method for controlling an electrophoresis process in accordance with aspects of the present disclosure.

FIG. 46 is a flowchart of a method 10000 for controlling an electrophoresis apparatus having a gel matrix disposed between electrodes for separation of particles along with a tracking dye in accordance with aspects of the present disclosure. The method includes at 10100, emitting a beam of light from the light emitter onto a first side of the gel matrix to illuminate a portion of the gel matrix, at 10200, receiving light from the illuminated gel matrix in a light receiver, and at 10300, monitoring a change in the light from the illuminated gel matrix due to migration of the tracking dye into the illuminated gel matrix and received by the light receiver. At least one of the light emitter and the light receiver includes a light guide having a first end and a second end. The first end is disposed adjacent to the gel matrix and the second end is disposed remotely from the gel matrix.

From the present description, it will be appreciated that while the two LEDs may be employed, one for transmitting light and the other for receiving light, the detection of light may be by a photodiode or other light detectors.

Suitable photodiodes include photodiodes SFH213 (OSRAM-opto-Semiconductors, Northville, Mich.) and OP906 (Optec, Lowell, Mich.) which have high sensitivity, and a moderate size and shape making them suitable for a compact sensor design. Suitable LEDs include LEDs WP7113SEC/J4 and WP710A10SEC/J4 (KingBright, City of Industry, Calif.) which work well with the two typically used dyes, namely bromophenol blue and xylene cyanol.

In various embodiments, the controller may be operable to control at least one of a visible alarm, an audio alarm, a telephone call, an email, and a text message upon the change in the light from the gel matrix due to migration of the tracking dye into the illuminated gel matrix. The controller may include a wireless transmitter for sending at least one of a telephone call, an email, and a text message upon the change in the light from the gel matrix due to migration of the tracking dye into the illuminated gel matrix.

In some embodiments, the controller may be operable, after detecting the dye, to alternate the voltage applied to the gel matrix so that the dye remains generally stationary. For example, a first voltage to the electrodes may be operably applied during monitoring the change in the light from the gel matrix due to migration of the tracking dye into the illuminated gel matrix, and a second voltage may be applied to the electrodes to maintain the generally stationary tracking dye. The first voltage may different from the second voltage. For example, the first voltage may be greater than the second voltage. In other embodiments, the second voltage may be an alternating voltage. The controller may be operable for turning off electrical power to the power supply based on a change in the light from the gel matrix due to migration of the tracking dye into the illuminated gel matrix.

It will also be appreciated that the sensor for the vertical electrophoresis systems overcomes the problem of obtaining reliable signals of the position of the tracking dye. For example, submersing a portion of the sensor into the buffer allows mounting the sensor close enough to the gel to receive a reliable signal from the migrating dye. The light guide such as a fiber optic cable is not affected by the electrical current generated by the buffer while it is submerged. The light source may be waterproofed and shielded which also allows contact with and submersion into the buffer. In addition, two fuses may be wired in series with the light sources disposed in the buffer solution in order to protect the circuit, e.g., to inhibit the likelihood of damage to the controller in case of any electrical fault. As noted above, such shielding and waterproofing may be avoided by employing sensors having two light guides.

From the present description, it will be appreciated that the electrophoresis controllers may be a standalone system operably attachable to a power supply, or may be an integrated device which includes a power supply. For example, the electrophoresis controller of FIG. 26 may be configured as an integrated device, and the electrophoresis controller of FIG. 29 may be configured as a standalone device operably attachable to a power supply. The light guide may be other light transmitting devices such as light tubes, light pipes, transparent hollow light guides, and fabricated from a plastic or other suitable material.

It is to be understood that the above description is intended to be illustrative, and not restrictive. For example, the above-described embodiments and/or aspects thereof may be used in combination with each other. In addition, many modifications may be made to adapt a particular situation or material to the teachings of the various embodiments without departing from their scope.

While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. An electrophoresis controller for use with an electrophoresis apparatus having a gel matrix disposed between electrodes for separation of particles along with an optical marker, said electrophoresis controller comprising:
   a sensor system comprising:
      a support having a first portion positionable on a first side of the gel matrix and a second portion positionable adjacent a second side of the gel matrix;
      a light emitter positioned on said first portion of said support for emitting light onto one side of the gel matrix;
      a light receiver positioned on said second portion of said support adjacent to the other side of the gel matrix for receiving emitted light passing through said gel matrix;
      at least one of said light emitter and said light receiver comprising a light guide having a first end and a second end, said first end being positioned on said support and facing the gel matrix, and said second end positioned remote from said sensor system;

a controller operably connected to said sensor system for monitoring a change in the light from the illuminated gel matrix due to migration of the optical marker into the illuminated gel matrix and received by said light receiver; and wherein said light guide comprises a fiber optic cable, said first end of said fiber optic cable being positioned on said support and facing the gel matrix, and said second end of the fiber optic cable operably connected to said controller remote from said sensor system.

2. The electrophoresis controller of claim 1 wherein said light emitter comprises a light source, said light receiver comprises said light guide, said first end of said light guide positioned on said second portion of said support, and said controller comprising a light detector operable for receiving light from said second end of said light guide for detecting light from the illuminated gel matrix.

3. The electrophoresis controller of claim 1 wherein said light emitter comprises said light guide, said first end of said light guide positioned on said first portion of said support, said controller comprising a light source operable for directing light into said second end of said light guide for illuminating the gel matrix, said light receiver comprising a second light guide, a first end of said second light guide positioned on said second portion of said support, and said controller comprising a light detector operable for receiving light from said second end of said second light guide for detecting light from the illuminated gel matrix.

4. The electrophoresis controller of claim 1 wherein said light emitter comprises said light guide, said first end of said light guide positioned on said first portion of said support, said controller comprising a light source operable for directing light into said second end of said light guide for illuminating the gel matrix, said light receiver comprising a light detector positioned on said second portion of said support adjacent to the other side of the gel matrix for receiving light from said light source passing through said gel matrix.

5. The electrophoresis controller of claim 4 wherein said light receiver comprises at least one of said light receiver comprising a light emitting diode employed as a photodetector.

6. The electrophoresis controller of claim 1 wherein at least one of said light emitter and said controller comprises a first light emitting diode operable to emit a first color, and at least one of said light receiver and said controller comprises a second light emitting diode employed as a photodetector, and wherein said first light emitting diode is operable to emit a first color, and said second light emitting diode is operable to emit a second color, and said first color being different from said second color.

7. The electrophoresis controller of claim 1 wherein said controller comprises a light emitting diode employed as a photodetector, and said light emitting diode operable for receiving light from said second end of said light guide for detecting light from the illuminated gel matrix.

8. The electrophoresis controller of claim 1 wherein the optical marker comprises a tracking dye.

9. The electrophoresis controller of claim 1 wherein said controller is operable, after detecting the optical marker, to control the voltage applied to the gel matrix so that the optical marker remains generally stationary.

10. The electrophoresis controller of claim 9 wherein said controller is operable to control a first voltage to the electrodes during monitoring the change in the light from the gel matrix due to migration of the optical marker into the illuminated gel matrix, and a second voltage with alternating polarity to the electrodes to maintain the optical marker generally stationary.

11. The electrophoresis controller of claim 9 wherein said controller is operable to control a first voltage to the electrodes during monitoring the change in the light from the gel matrix due to migration of the optical marker into the illuminated gel matrix, and a second voltage to the electrodes to maintain the optical marker generally stationary, and wherein the first voltage is different from the second voltage.

12. The electrophoresis controller of claim 1 further comprising a wireless transmitter for sending at least one of a telephone call, a text message, and an email upon the change in the light from the gel matrix between said light emitter and said light receiver due to migration of the optical marker into the illuminated gel matrix.

13. The electrophoresis controller of claim 1 wherein said controller is operable to control at least one of a visible alarm, an audio alarm, a telephone call, a text message, and an email upon the change in the light from the gel matrix due to migration of the optical marker into the illuminated gel matrix.

14. The electrophoresis controller of claim 1 wherein said controller is operable for turning off electrical power to a power supply based on a change in the light from the gel matrix between said light emitter and said light receiver due to migration of the optical marker into the illuminated gel matrix.

15. The electrophoresis controller of claim 1 wherein said controller comprises an electrical plug electrically connectable to a power source for receiving electrical power, and an electrical socket electrically connectable to an electrical plug of a power supply.

16. The electrophoresis controller of claim 1 further comprising a power supply.

17. A method for controlling an electrophoresis apparatus having a gel matrix disposed between electrodes for separation of particles along with an optical marker, the method comprising:
providing the electrophoresis controller of claim 1;
emitting a beam of light from the light emitter onto a first side of the gel matrix to illuminate a portion of the gel matrix;
receiving light from the illuminated gel matrix in a light receiver; and
monitoring the received light in the controller.

18. A sensor system for use with an electrophoresis apparatus having a vertically-extending gel matrix disposed between electrodes for separation of particles along with an optical marker, said sensor comprising:
a support having a first portion positionable on a first side of the gel matrix and a second portion positionable adjacent a second side of the gel matrix;
a light emitter positioned on said first portion of said support for emitting light onto one side of the gel matrix;
a light receiver positioned on said second portion of said support adjacent to the other side of the gel matrix for receiving emitted light from said light source passing through said gel matrix;
a mounting clip having a first portion supportable on the electrophoresis apparatus and a second portion releasably attachable to said support to position said light emitter and said light receiver vertically and horizontally along the vertically-extending gel matrix; and at least one of said light emitter and said light receiver comprising a fiber optic cable having a first end and a second end, said first end being positioned on said support and facing the gel matrix, and said second end being remote from said sensor system.

19. The sensor system of claim 18 wherein said light receiver comprises said fiber optic cable, and said second portion of said support comprises a shield for shielding ambient light from said first end of said fiber optic cable.

20. The sensor system of claim 18 wherein said support comprises a passageway through which said first end of said fiber optic cable is positionable, and wherein said first end of said fiber optic cable is positionable prior to an opening of said passageway.

21. The sensor system of claim 18 wherein said support comprises a generally C-shaped configuration or U-shaped configuration.

22. The sensor system of claim 18 wherein said first end of said fiber optic cable is disposable in a buffer of said electrophoresis apparatus.

23. The sensor system of claim 18 wherein a portion of said first portion of said support and said first end of said fiber optic cable are disposable in a buffer in said electrophoresis apparatus.

24. The sensor system of claim 18 wherein said light emitter and said light receiver are disposable in a buffer in said electrophoresis apparatus.

25. The sensor system of claim 18 wherein the optical maker comprises a tracking dye.

26. The sensor system of claim 18 wherein at least one of said light emitter and said light receiver comprises a light emitting diode.

27. The sensor system of claim 18 further comprising the electrophoresis apparatus.

28. A method for controlling an electrophoresis apparatus having a gel matrix disposed between electrodes for separation of particles along with an optical marker, the method comprising:
    emitting a beam of light from the light emitter onto a first side of the gel matrix to illuminate a portion of the gel matrix;
    receiving light from the illuminated gel matrix in a light receiver, at least one of the light emitter and the light receiver comprising a light guide having a first end and a second end, the first end of the light guide disposed adjacent to the gel matrix and the second end of the light guide disposed remotely from the gel matrix;
    monitoring a change in the light from the illuminated gel matrix due to migration of the optical marker into the illuminated gel matrix and received by the light receiver; and
    wherein at least one of the emitting light or receiving light comprises disposing the first end of the light guide in a buffer solution.

29. The method of claim 28 wherein the receiving further comprises detecting the light with a light emitting diode employed as a photodiode.

30. The method of claim 28 wherein the emitting comprises emitting light from a first light emitting diode, and the receiving light comprises detecting light with a light emitting diode employed as a photodetector, and wherein the first light emitting diode is operable to emit a first color, the second light emitting diode is operable to emit a second color, and the first color being different from the second color.

31. The method of claim 28 wherein the optical marker comprises a tracking dye.

32. The method of claim 28 further comprising turning off a power supply providing electrical power to the electrophoresis apparatus based on the monitored change in the light due to migration of the optical marker into the illuminated gel matrix.

33. The method of claim 28 further comprising controlling a voltage applied to the gel matrix based on the monitored detected light due to migration of the optical marker into the illuminated gel matrix so that the optical marker remains generally stationary.

34. The method of claim 33 wherein the controlling the voltage comprises applying a first voltage to the electrodes for monitoring migration of the optical marker into the illuminated gel matrix, and applying a second voltage to the electrodes to maintain the generally stationary optical marker, and wherein the first voltage is different from the second voltage.

35. The method of claim 28 wherein the light guide comprises a fiber optic cable.

36. The method of claim 28 further comprising activating at least one of a visible alarm, an audio alarm, a telephone call, a text message, and an email upon the change in the light from the gel matrix due to migration of the optical marker into the illuminated gel matrix.

37. A method for controlling an electrophoresis apparatus having a gel matrix disposed between electrodes for separation of particles along with an optical marker, the method comprising:
    emitting a beam of light from the light emitter onto a first side of the gel matrix to illuminate a portion of the gel matrix;
    receiving light from the illuminated gel matrix in a light receiver;
    monitoring a change in the light from the illuminated gel matrix due to migration of the optical marker into the illuminated gel matrix and received by the light receiver;
    controlling a voltage applied to the gel matrix based on the monitored detected light due to migration of the optical marker into the illuminated gel matrix so that the optical marker remains generally stationary; and
    wherein the controlling the voltage comprises applying a first voltage to the electrodes for monitoring migration of the optical marker into the illuminated gel matrix, and applying a second voltage to the electrodes to maintain the generally stationary optical marker, and wherein the first voltage is different from the second voltage.

38. The method of claim 37 wherein the receiving further comprises detecting the light with a light emitting diode employed as a photodiode.

39. The method of claim 37 wherein the emitting comprises emitting light from a first light emitting diode, and the receiving light comprises detecting light with a light emitting diode employed as a photodetector, and wherein the first light emitting diode is operable to emit a first color, the second light emitting diode is operable to emit a second color, and the first color being different from the second color.

40. The method of claim 37 wherein at least one of the light emitter and the light receiver comprising a light guide having a first end and a second end, the first end of the light guide disposed adjacent to the gel matrix and the second end of the light guide disposed remotely from the gel matrix.

41. The method of claim 40 wherein at least one of the emitting light or receiving light comprises disposing the first end of the light guide in a buffer solution.

42. The method of claim 40 wherein the light guide comprises a fiber optic cable.

43. The method of claim 37 further comprising turning off a power supply providing electrical power to the electrophoresis apparatus based on the monitored change in the light due to migration of the optical marker into the illuminated gel matrix.

44. The method of claim 37 further comprising activating at least one of a visible alarm, an audio alarm, a telephone call, a text message, and an email upon the change in the light from the gel matrix due to migration of the optical marker into the illuminated gel matrix.

\* \* \* \* \*